United States Patent
Whitehurst et al.

(10) Patent No.: US 9,452,288 B2
(45) Date of Patent: Sep. 27, 2016

(54) MULTIMODAL NEUROSTIMULATION SYSTEMS AND METHODS

(75) Inventors: Todd Whitehurst, Valencia, CA (US); Rafael Carbunaru, Valley Village, CA (US); Kristen Jaax, Santa Clarita, CA (US); Andrew DiGiore, Santa Monica, CA (US); Brett D Schleicher, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 2782 days.

(21) Appl. No.: 11/951,987

(22) Filed: Dec. 6, 2007

(65) Prior Publication Data

US 2009/0149917 A1    Jun. 11, 2009

(51) Int. Cl.
| | |
|---|---|
| A61N 1/00 | (2006.01) |
| A61N 1/36 | (2006.01) |
| A61N 1/372 | (2006.01) |
| A61B 18/12 | (2006.01) |
| A61N 1/37 | (2006.01) |

(52) U.S. Cl.
CPC ....... *A61N 1/36017* (2013.01); *A61N 1/37247* (2013.01); *A61B 18/12* (2013.01); *A61N 1/37* (2013.01); *A61N 1/37211* (2013.01); *A61N 1/37241* (2013.01); *A61N 1/37288* (2013.01)

(58) Field of Classification Search
None
See application file for complete search history.

(56) References Cited

U.S. PATENT DOCUMENTS

| | | |
|---|---|---|
| 6,393,325 B1 | 5/2002 | Mann et al. |
| 6,609,032 B1 | 8/2003 | Woods et al. |
| 6,909,917 B2 | 6/2005 | Woods et al. |
| 7,187,978 B2 | 3/2007 | Malek et al. |
| 7,212,133 B2 | 5/2007 | Goetz et al. |
| 7,359,751 B1 | 4/2008 | Erickson et al. |

(Continued)

FOREIGN PATENT DOCUMENTS

| | | |
|---|---|---|
| WO | WO 02/09808 A1 | 2/2002 |
| WO | WO 2007/016184 A1 | 2/2007 |

OTHER PUBLICATIONS

PCT International Preliminary Report on Patentability (Chapter I of the Patent Cooperation Treaty) for PCT/US2008/085696, Applicant: Boston Scientific Neuromodulation Corporation, Form PCT/IB/326 and 373, dated Jun. 17, 2010 (9 pages).

(Continued)

*Primary Examiner* — Christopher D Koharski
*Assistant Examiner* — Elizabeth K So
(74) *Attorney, Agent, or Firm* — Schwegman Lundberg & Woessner, P.A.

(57) ABSTRACT

A system for performing a neurostimulation trial comprises an external trial stimulator capable of delivering stimulation energy to a plurality of electrodes carried by one or more stimulation leads. The external trial stimulator is configurable to operate in a plurality of stimulation energy delivery modes to respectively emulate one of different neurostimulator types. The system may further comprise a programmer capable of configuring the external trial stimulator to operate in one of the stimulation energy delivery modes. The programmer may be capable of generating a first programming screen capable of allowing a first set of stimulation parameters to be defined for the first neurostimulator type, and a second programming screen capable of allowing a second set of stimulation parameters to be defined for a second neurostimulator type.

28 Claims, 13 Drawing Sheets

(56) References Cited

U.S. PATENT DOCUMENTS

| | | |
|---|---|---|
| 7,680,540 B2 * | 3/2010 | Jensen et al. .................. 607/60 |
| 2002/0002372 A1 * | 1/2002 | Jahns et al. .................... 606/41 |
| 2004/0059395 A1 | 3/2004 | North et al. |
| 2004/0111130 A1 | 6/2004 | Hrdlicka et al. |
| 2006/0247739 A1 | 11/2006 | Wahlstrand et al. |
| 2007/0038250 A1 | 2/2007 | He et al. |

OTHER PUBLICATIONS

PCT International Search Report for PCT/US2008/085696, Applicant: Boston Scientific Neuromodulation Corporation, Form PCT/ISA/210 and 220, dated Apr. 1, 2009 (8 pages).

PCT Written Opinion of the International Search Authority for PCT/US2008/085696, Applicant: Boston Scientific Neuromodulation Corporation, Form PCT/ISA/237, dated Apr. 1, 2009 (7 pages).

* cited by examiner

| PATIENT INFORMATION SCREEN | | | | 142 |
|---|---|---|---|---|

PATIENT NAME: JOHN DOE          TIME INTERVAL:   EVERY 2 hours
SEX:           MALE                              FOR 15 MINUTES
HEIGHT:        5' 11"
WEIGHT:        185 lbs          BATTERY USAGE:   55%
SYMPTOMS:      CHRONIC PAIN IN  CASE HISTORY:    HEART ATTACK 2001
               RIGHT LEG                         DIABETES 2000
CLINICIAN:     DR. GRAY                          BROKEN LEG 2005

CLINIC:        ABC CLINIC

IPG:           ADVANCED BIONICS
               PRECISION™

STIMULATION
SETTINGS:      E2(+,1mA); E3 (+,2mA)
               E6(-:1.6mA); E7(-,1.5mA);
               150 PPS; 50 µS

FIG. 8

THERAPEUTIC DEVICE SELECTION SCREEN — 144

146 — ☐ FIRST IPG PROGRAMMER
148 — ☐ SECOND IPG PROGRAMMER
150 — ☐ THIRD IPG PROGRAMMER
152 — ☐ RF ABLATION CONTROLLER
154 — ☐ MEDTRONIC SYNCHROMED™ DRUG PUMP

FIG. 9

MULTIMODAL NEUROSTIMULATION SYSTEMS AND METHODS

FIELD OF THE INVENTION

The present invention relates to tissue stimulation systems, and more particularly, to systems and methods for trialing different types of tissue stimulation systems.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoris and incontinence. Deep Brain Stimulation (DBS) has also been applied therapeutically for well over a decade for the treatment of movement disorders and epilepsy. Further, in recent investigations Peripheral Nerve Stimulation (PNS) systems have demonstrated efficacy in the treatment of chronic pain syndromes, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Various of these implantable neurostimulation systems typically include one or more electrode-carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the electrode(s) to stimulate the tissue and provide the desired efficacious therapy to the patient. A handheld patient programmer may be utilized to remotely instruct the neurostimulator to generate electrical stimulation pulses in accordance with selected parameters or stimulation sets. The handheld programmer may, itself, be programmed by a technician attending the patient, for example, by using a Clinician's Programmer Station (CPS), which typically includes a general purpose computer, such as a laptop, with a programming software package installed thereon. The CPS may also be used to program the neurostimulator directly.

In a typical procedure, such as an SCS procedure, the stimulation lead(s) are introduced into the patient in contact with the target tissue under fluoroscopy. After proper placement of the lead(s) at the target area of the spinal cord, the lead(s) are anchored in place, and the proximal ends of the lead(s), or alternatively lead extensions, are passed through a tunnel leading to a subcutaneous pocket (typically made in the patient's abdominal or buttock area) where a neurostimulator is implanted. The lead(s) are connected to the neurostimulator, which is programmed with the stimulation parameter set(s). Using the CPS and/or handheld patient programmer, the neurostimulator may be operated to test the effect of stimulation and, if necessary, adjust the programmed set(s) of stimulation parameters for optimal therapy based on verbal feedback from the patient. Based on this feedback, the lead position(s) may also be adjusted and re-anchored if necessary. Any incisions are then closed to fully implant the system.

Prior to permanent implantation of the neurostimulator (as described above), the patient will typically undergo a neurostimulation trial period, which involves a brief test stimulation period in the operating room and an evaluation period of several days at home. During the test stimulation period in the operating room, stimulation energy may be delivered to the electrodes of the lead(s), while the patient provides verbal feedback regarding the efficacy of the stimulation, to verify that the lead(s) are stimulating the target neural tissue. Stimulation energy is also delivered to the electrodes at this time to formulate the most effective set of stimulus parameters, which include the electrodes that are sourcing (anodes) or returning (cathodes) the stimulation pulses at any given time, as well as other parameters, such as the magnitude, duration, and frequency of the stimulation pulses. The best stimulus parameter set will typically be one that provides stimulation energy to all of the target tissue that must be stimulated in order to provide the therapeutic benefit (e.g., pain relief), yet minimizes the volume of non-target tissue that is stimulated.

Rather than using the implantable neurostimulator to deliver the stimulation energy to the lead(s), the trial is typically performed with the use of an external trial stimulator (ETS), which provides the same stimulation functionality as the implantable neurostimulator, but is intended to be worn by the patient during the evaluation period at home. The CPS may be utilized to modify the characteristics of the stimulation output by the ETS, and to ultimately program the ETS in accordance with the selected parameters or stimulation sets.

As a result of the fast growing SCS market and neuromodulation market in general, several different neurostimulators have been developed both across the entire market and within each company. Thus, the physician often has a multitude of available neurostimulators from which to select, any of which may provide the optimum treatment for the patient. For example, Advanced Bionics Corporation markets a Precision® neurostimulator, is in clinical trial with the Bion® microstimulator, and is developing a multi-electrode Bion® microstimulator. Medtronic, Inc. markets a Synergy® neurostimulator and a Restore® neurostimulator. Advanced Neuromodulation Systems markets a Genesis® neurostimulator and an EON® neurostimulator.

Each of these devices requires its own ETS to optimize programming and replicate the appropriate implantable device. For example, the Precision® neurostimulator has a constant current source hardware platform with sixteen independent current sources that can independently deliver constant current at different magnitudes to any combination of electrodes over multiple channels. As another example, the Bion® microstimulator has a simpler, but smaller, constant current source hardware platform that can deliver current at equal magnitudes between two electrodes over a single channel. Both of the Synergy® and Restore® neurostimulators deliver electrical energy at a constant voltage, with the Synergy® neurostimulator having two voltage sources and the Restore® neurostimulator having a single voltage source. Both of the Genesis® and EON® neurostimulators have single constant current sources. As can be appreciated, all of these products require dedicated ETSs, and as such, there is no single ETS that can emulate all of these neurostimulators. In addition, the software package used by the CPS to program a particular ETS or associated neurostimulator has different features, parameters, structures, and abilities, and thus, different software packages are required for the ETSs and associated neurostimulators.

While the use of dedicated ETSs and programming software packages do not necessarily create a problem during the trialing period when it is known which type (make and/or model) of implantable neurostimulator will provide the best treatment solution for the patient at the beginning of the trial period, more likely than not, this information is not known. That is, the only realistic way to determine which neurostimulator is the best option is to actually perform a trial for each one on the patient. The current solution is to switch ETSs when trialing the devices in the operating room, and based on patient feedback, selecting the ETS, and thus, the neuromodulation device, that optimizes the therapy. In this manner, the patient need not schedule a return visit to the operating room or clinician's office to replace the ETS if the therapy is not optimum.

However, this requires the physician to maintain several ETSs in the operating room. In addition, after each ETS is switched, the corresponding programming software package must be opened (executed) on each CPS. Each programming software package takes time to load and configure, as the use of a new programming software package requires the re-entry of patient data. This, in addition to the physical switching of the ETSs, may add a significant amount of time to a given procedure, increasing the risk factors of the operation and decreasing patient and physician interest in the particular therapy intended to be delivered by the neurostimulation device.

There, thus, remains a need for an improved method and system for trialing different neurostimulation devices.

SUMMARY OF THE INVENTION

In accordance with a first aspect of the present inventions, an external trial stimulator is provided. The external trial stimulator (ETS) comprises one or more connectors capable of respectively mating with one or more stimulation leads carrying a plurality of electrodes, and a plurality of electrical terminals capable of electrically coupling the ETS to the plurality of electrodes via the connector(s). The external trial stimulator further comprises stimulation circuitry capable of delivering stimulation energy to the plurality of electrical terminals in accordance with a set of stimulation parameters (e.g., an electrode combination, pulse amplitude, pulse width, a pulse frequency, and a burst pattern). The external trial stimulator further circuitry capable of reconfiguring the stimulation circuitry to selectively emulate different neurostimulator types.

In one embodiment, the external trial stimulator comprises memory for storing the stimulation parameter set. In another embodiment, the external trial stimulator comprising telemetry circuitry capable of receiving instructions from a programmer (such as a CPS), wherein the circuitry is capable of reconfiguring the stimulation circuitry to selectively emulate different neurostimulator types in response to the instructions. The circuitry can emulate different neurostimulator types in any one or more of a variety of manners.

For example, the circuitry may emulate one of the different neurostimulator types by operating the stimulation circuitry to deliver the stimulation energy to the plurality of contacts at a constant voltage in response to varying impedance at the electrical terminals, and may emulate another one of the different neurostimulator types by operating the stimulation circuitry to deliver the stimulation energy to the electrical terminals at a constant current in response to varying impedance at the electrical terminals. In one embodiment, the stimulation circuitry comprises one or more current sources capable of outputting one or more constant currents to the plurality of electrical terminals. In this case, the external trial stimulator may comprise monitoring circuitry capable of measuring voltage at the plurality of electrical terminals, wherein the circuitry is capable of operating the stimulation circuitry to deliver the stimulation energy to the electrical terminals at the constant voltage by varying the current source(s) as the measured voltage varies. The circuitry may be capable of operating the stimulation circuitry to deliver the stimulation energy to the electrical terminals at the constant current by not varying the constant current source(s) as the measured voltage varies.

As another example, the circuitry may emulate one of the different neurostimulator types by operating the stimulation circuitry to deliver the stimulation energy at different magnitudes respectively to the electrical terminals, and may emulate another one of the different neurostimulator types by operating the stimulation circuitry to deliver the stimulation energy at a single magnitude to the plurality of electrical terminals.

As still another example, the circuitry may emulate one of the different neurostimulator types by operating the stimulation circuitry to deliver the stimulation energy to the electrical terminals in accordance with a plurality of stimulation parameter sets, and may emulate another one of the different neurostimulator types by operating the stimulation circuitry to deliver the stimulation energy to the electrical terminals in accordance with a single stimulation parameter set.

As yet another example, the circuitry may emulate one of the different neurostimulator types by operating the stimulation circuitry to deliver the stimulation energy between two or more of the electrical terminals, and may emulate another one the different neurostimulator types by operating the stimulation circuitry to only deliver the stimulation energy from one or more of the electrical terminals.

In accordance with a second aspect of the present inventions, a system for performing a neurostimulation trial is provided. The system comprises an external trial stimulator capable of delivering stimulation energy to a plurality of electrodes carried by one or more stimulation leads. In one embodiment, the stimulation lead(s) are not directly matable to the external trial stimulator, in which case, the system may further comprise a lead adapter capable of mating the stimulation lead(s) to the external trial stimulator.

The external trial stimulator is reconfigurable to operate in a plurality of stimulation energy delivery modes to respectively emulate one of different neurostimulator types. The system may optionally comprises a programmer capable of reconfiguring the external trial stimulator (e.g., wirelessly) to operate in one of the stimulation energy delivery modes. Alternatively, the external stimulator may be reconfigured directly without the use of a programmer. In one embodiment, the programmer is capable of reconfiguring the external trial stimulator in response to a user entry. The external trial stimulator can be reconfigured in different stimulation energy delivery modes in any one or more of a variety of manners.

For example, the external trial stimulator is capable of delivering stimulation energy to the electrodes at a constant voltage when reconfigured to operate in a first one of several stimulation energy delivery modes, and is capable of delivering stimulation energy to the plurality of electrodes at a constant current when reconfigured to operate in a second one of several stimulation energy delivery modes. As another example, the external trial stimulator is capable of independently delivering stimulation energy to the electrodes when reconfigured to operate in a first one of several stimulation energy delivery modes, and is capable of uniformly delivering stimulation energy to the electrodes when reconfigured to operate in a second one of several stimulation energy delivery modes. As still another example, the external trial stimulator is capable of delivering stimulation energy to the electrodes over multiple channels when reconfigured to operate in a first one of several stimulation energy delivery modes, and is capable of delivering stimulation energy to the electrodes over a single channel when reconfigured to operate in a second one of several stimulation energy delivery modes. As yet another example, the external trial stimulator is capable of delivering stimulation energy to the electrodes in a multipolar manner when reconfigured to operate in a first one of several stimulation energy delivery modes, and is capable of delivering stimulation energy to the electrodes in a monopolar manner when reconfigured to operate in a second one of several stimulation energy delivery modes. Each of the several stimulation energy delivery modes may have a combination of mutually exclusive features or may only have a single feature.

In an optional embodiment, the external trial stimulator is capable of modifying the stimulation energy delivered to the electrodes during emulation of each of the different neurostimulator types, and the programmer is capable of controlling the modification of the stimulation energy. In another optional embodiment, the programmer is capable of performing a therapeutic comparative analysis between the different neurostimulator types based on the emulation of the different neurostimulator types by the external trial stimulator. In another optional embodiment, the external trial stimulator is capable of delivering ablation energy to the electrodes, and the programmer is capable of initiating delivery of the ablation energy from the external trial stimulator to the electrodes.

In accordance with a third aspect of the present inventions, a method of performing a neurostimulation trial is provided. The method comprises introducing one or more stimulation leads carrying a plurality of electrodes into a patient, and coupling an external trial stimulator to the stimulation lead(s). The method further comprises configuring the external trial stimulator to emulate a first neurostimulator type while delivering stimulation energy from the external trial stimulator to the electrodes, and configuring the external trial stimulator to emulate a second neurostimulator type while delivering stimulation energy from the external trial stimulator to the electrodes.

The first and second neurostimulators may be emulated in any one or more of a variety of manners. For example, the external trial stimulator may be operated to deliver the stimulation energy to the electrodes at a constant voltage to emulate the first neurostimulator type, and operated to deliver the stimulation energy to the electrodes at a constant current to emulate the second neurostimulator type. As another example, the external trial stimulator may be operated to independently deliver the stimulation energy to the electrodes to emulate the first neurostimulator type, and operated to uniformly deliver the stimulation energy to the electrodes to emulate the second neurostimulator type. As still another example, the external trial stimulator may be operated to deliver the stimulation energy to the electrodes over a multiple of channels to emulate the first neurostimulator type, and operated to deliver the stimulation energy to the electrodes over a single channel to emulate the second neurostimulator type. As yet another example, the external trial stimulator may be operated to deliver the stimulation energy to the electrodes in a multipolar manner to emulate the first neurostimulator type, and operated to deliver the stimulation energy to the electrodes in a monopolar manner to emulate the second neurostimulator type.

One method further comprises modifying the stimulation energy delivered from the external trial stimulator to the electrodes during emulation of each of the first and second neurostimulator types. An optional method comprises performing a therapeutic comparative analysis between the first and second neurostimulator types based on the emulation of the first and second neurostimulator types by the external trial stimulators. In another method, one of the first and second neurostimulator types is selected based on the therapeutic comparative analysis, and a neurostimulator corresponding to the selected neurostimulator type is permanently implanted into the patient. Alternatively, neurostimulators corresponding to multiple neurostimulator types can be permanently implanted into the patient.

In accordance with a fourth aspect of the present inventions, a computer executable software program stored on a medium is provided. The software program comprises a first neurostimulator programming module capable of generating at least a first set of stimulation parameters for use by a first neurostimulator type, and a second neurostimulator programming module capable of generating at least a second set of stimulation parameters for use by a second neurostimulator type. The software program further comprises a therapeutic device selection module configured for selecting one of the first and second neurostimulator programming modules in response to a user input.

The stimulation parameters for the different neurostimulator types can differ in any one or more of a variety of manners. For example, the first simulation parameter set(s) may define a stimulation current value of at least one electrode, and the second stimulation parameter set(s) may define a stimulation current voltage value for at least one electrode. As another example, the first stimulation parameter set(s) may define independent stimulation amplitude values (either absolute or fractionalized) for a plurality of electrodes, and the second stimulation parameter set(s) may define a single stimulation amplitude value for a plurality of electrodes. As still another example, the first stimulation parameter set(s) may define multiple channels for a plurality of electrodes, and the second stimulation parameter set(s) may define a single channel for a plurality of electrodes. As yet another example, the first stimulation parameter set(s) may define a multipolar electrode configuration, and the second stimulation parameter set(s) may define a monopolar electrode configuration.

In one embodiment, first and second neurostimulator programming modules are capable of generating the first and second stimulation parameter sets in response to user inputs. In another embodiment, the first and second neurostimulator programming modules are capable of generating the first and second stimulation parameter sets in accordance with user-defined inputs. In an optional embodiment, the software program further comprises a comparative therapeutic analysis module capable of performing a therapeutic comparative analysis between the first and second neurostimulator types based on stimulation energy delivered to a patient by the emulation of the first and second neurostimulator types in accordance with the respective first and second stimulation parameter sets. In another optional embodiment, the software program comprises a therapeutic ablation module capable of generating a set of ablation parameters for use by an ablation device, wherein the therapeutic device selection module is capable of selecting the therapeutic ablation module in response to another user input. In yet another optional embodiment, the software program further comprises a drug pump programming module capable of generating a set of drug delivery parameters for use by an implantable drug pump, wherein the therapeutic device selection module is capable of selecting the drug pump programming module in response to another user input.

In accordance with a fifth aspect of the present inventions, a programmer for an external trial stimulator is provided. The programmer comprises a user interface having a monitor and an input device. The programmer further comprises a processor capable of generating a first programming screen for a first neurostimulator type for display on the monitor, and generating a second programming screen for a second neurostimulator type for display on the monitor. The first programming screen is capable of allowing a first set of stimulation parameters to be defined via the input device for the first neurostimulator type, and the second programming screen is capable of allowing a second set of stimulation parameters to be defined for the second neurostimulator type. The programmer further comprises output circuitry (e.g., telemetry circuitry) for transmitting the first and second stimulation parameter sets.

The first and second programming screens may differ from each other in any one of a variety of manners. For example, the programming screen may only allow a stimulation current value to be defined via the input device for the first neurostimulator type, and the second programming screen may only allow a stimulation voltage value to be defined via the input device for the second neurostimulator type. As another example, the first programming screen may allow stimulation amplitude values (either absolute or fractionalized) to be independently defined via the input device for the first neurostimulator type, and the second programming screen may only allow a stimulation amplitude value to be uniformly defined via the input device for the second neurostimulator type. As still another example, the first programming screen may allow multiple channels to be defined via the input device for the first neurostimulator type, and the second programming screen may only allow a single channel to be defined via the input device for the second neurostimulator type. As yet another example, the first programming screen may allow a multipolar configuration to be defined via the input device for the first neurostimulator type, and the second programming screen may only allow a monopolar configuration to be defined via the input device for the second neurostimulator type.

In an optional embodiment, the circuitry is capable of generating a therapeutic ablation screen for display on the monitor, which allows a set of ablation parameters to be defined via the input device for an ablation device. In another optional embodiment, the circuitry is capable of generating a drug delivery programming screen for display on the monitor, which allows a set of drug delivery parameters to be defined via the input device for a drug delivery device.

Other and further aspects and features of the inventions will be evident from reading the following detailed description of the preferred embodiments, which are intended to illustrate, not limit, the inventions.

BRIEF DESCRIPTION OF THE DRAWINGS

The drawings illustrate the design and utility of preferred embodiments of the present inventions, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the inventions and are not therefore to be considered limiting of its scope, the inventions will be described and explained with additional specificity and detail through the use of the accompanying drawings in which:

FIG. 8 is an exemplary patient information screen generated by the CPS of FIG. 7;

FIG. 9 is an exemplary therapeutic device selection screen generated by the CPS of FIG. 7;

DETAILED DESCRIPTION OF THE EMBODIMENTS

At the outset, it is noted that the present invention may be used with an implantable pulse generator (IPG), radio frequency (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical or deep brain stimulator, peripheral nerve stimulator, a microstimulator, or in any other neural stimulator configured to treat urinary incontinence, sleep apnea, shoulder sublaxation, etc.

Figure 1:
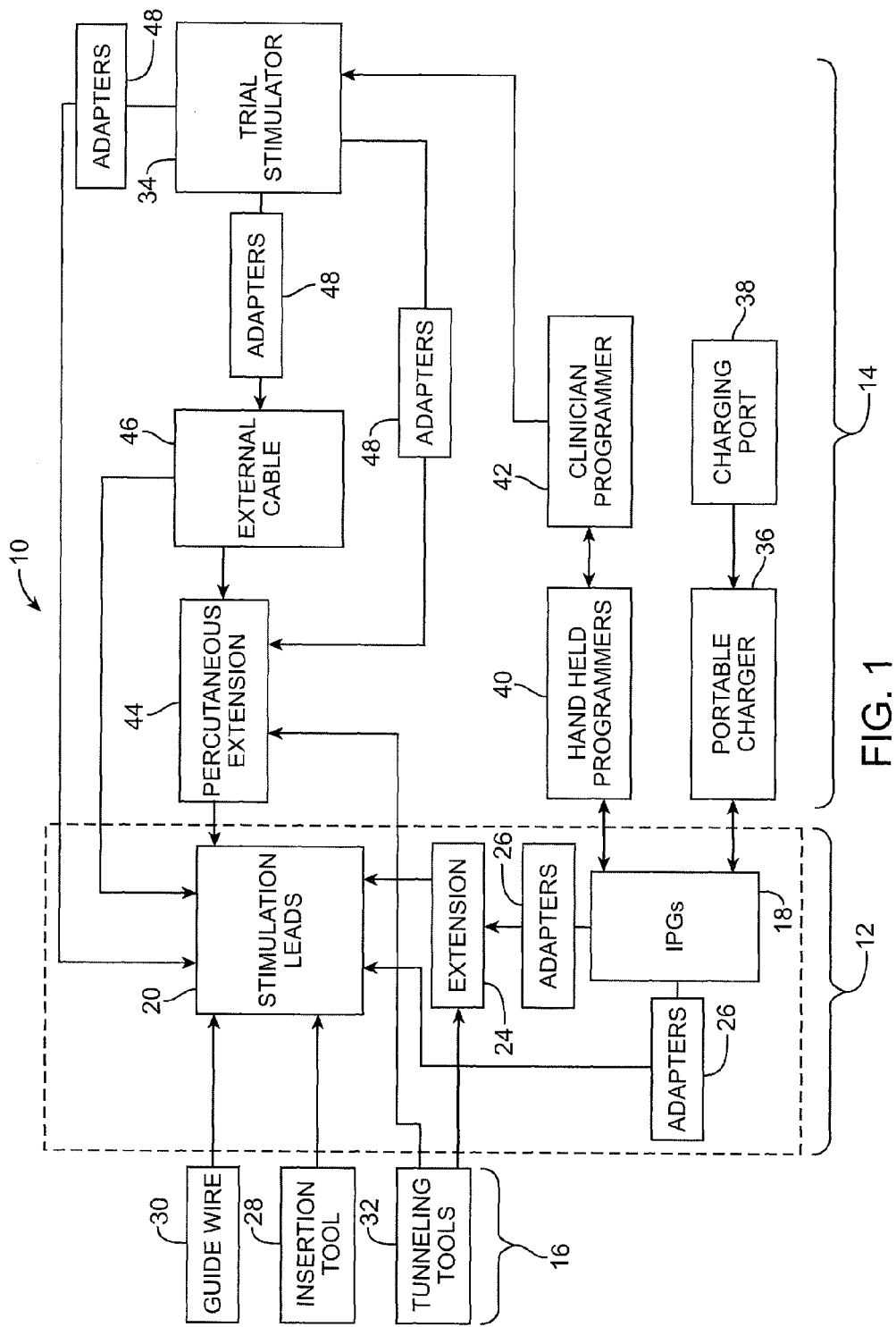
FIG. 1 is a block diagram of one embodiment of a spinal cord stimulation (SCS) kit arranged in accordance with the present inventions.
Figure 2:
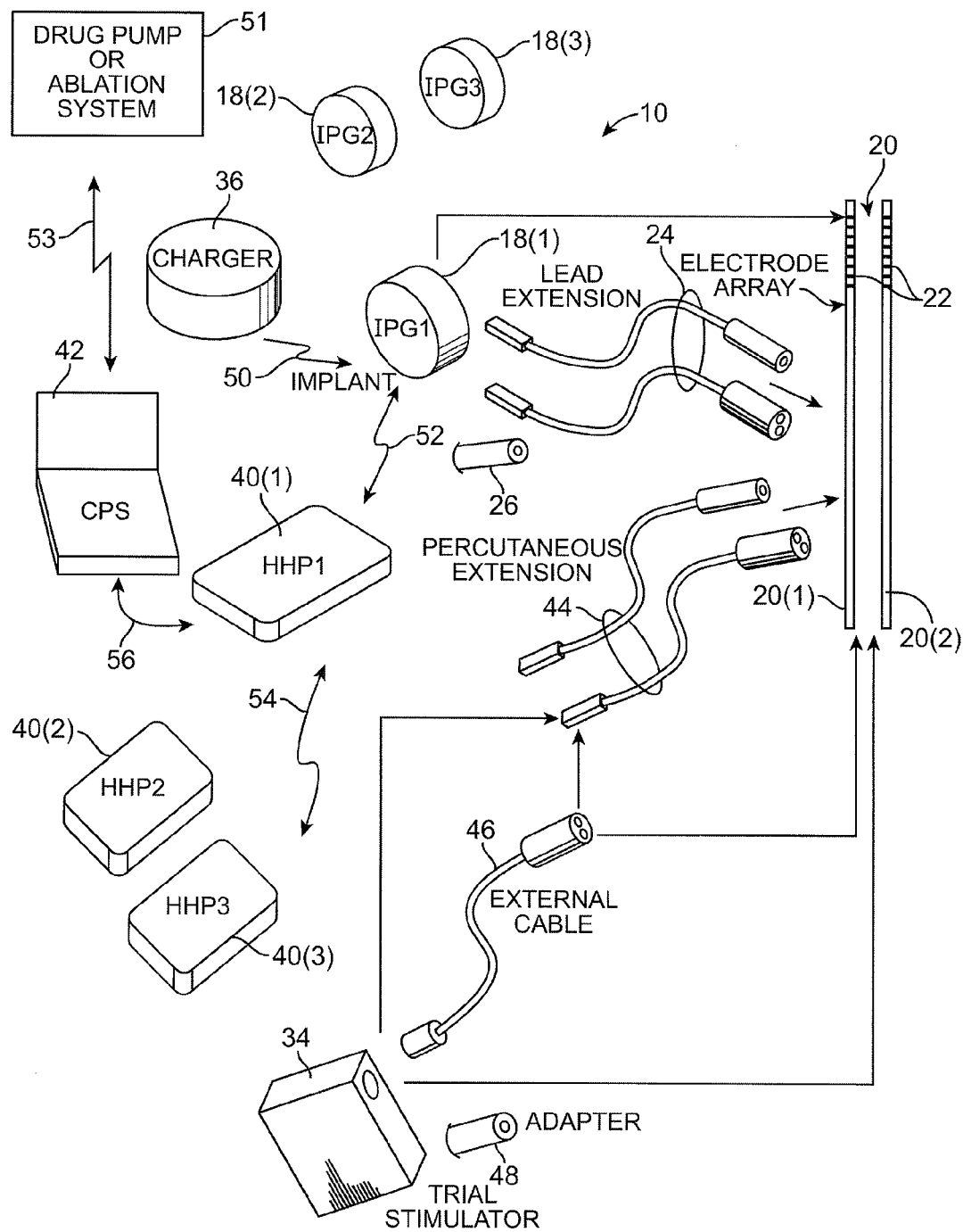
FIG. 2 is a perspective view of the SCS kit of FIG. 1.
Figure 3:
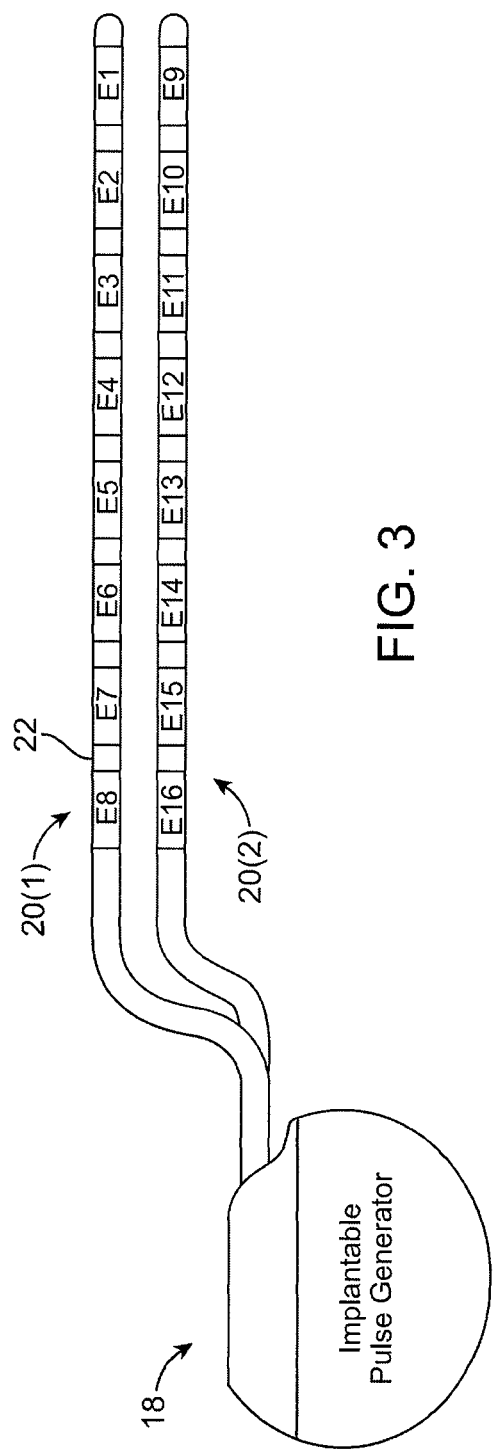
FIG. 3 is a plan view of an implantable pulse generator (IPG) and stimulation leads used in the SCS kit of FIG. 1.

Turning first to FIGS. 1-3, an exemplary SCS kit 10 arranged in accordance with one embodiment of the present inventions will be described. The kit 10 comprises components that may be subdivided into three broad categories: (1)

implantable components 12; (2) external components 14; and (3) surgical components 16. The implantable components 12 include a plurality of different implantable neurostimulators in the form of implantable pulse generators (IPGs) 18, one or more stimulation leads 20 carrying an array of electrodes 22 (shown in FIG. 2), a lead extension 24 (as needed), and one or more lead adapters 26 (as needed).

In the illustrated embodiment, the stimulation leads 20 are pecutaneous leads, and to this end, the electrodes 22 are arranged in-line along the stimulation leads 20. Alternatively, the stimulation leads 20 may be replaced with a single paddle stimulation lead. In the illustrated embodiment shown in FIG. 3, the first stimulation lead 20(1) has eight electrodes 22 (labeled E1-E8), and the second stimulation lead 20(2) includes eight electrodes 22 (labeled E9-E16). The actual number of leads and electrodes will, of course, vary according to the intended application.

Any of the IPGs 18 can provide electrical stimulation through at least some of the sixteen electrodes $E_1$ through $E_{16}$ included within the electrode arrays 22. To this end, each of the IPGs 18 may be connected directly to the stimulation leads 20, or indirectly to stimulation leads 20 via the lead extension 26. Each of the IPGs 18 includes stimulating electrical circuitry, processing circuitry, a power source (e.g., a rechargeable battery) or receiver, and telemetry circuitry, all contained within a hermetically sealed, biocompatible, case. For purposes of brevity, the components of the IPGs 18 will not be described in detail herein. The IPGs 18 are all different from each other in that they can be categorized into different types that can be trialed to determine the most effective IPG 18 to be implanted within the patient. For the purposes of this specification, the term "different type" with respect to a neurostimulator device, such as an IPG, shall refer to different fundamental architectures of the stimulation circuitry contained in the neurostimulator device (such as those described below), as opposed to a differences (e.g., different number of electrodes) that do not impact the fundamental architecture of the stimulation circuitry contained in the neurostimulator device. Notably, the IPGs 18 are exemplary, and thus, other types or additional types of IPGs 18 can be provided. Only one of the IPGs 18 is designed to mate directly with the stimulation leads 20 and/or lead extension 24. The adapters 26 can be used to connect the other IPGs 18 to the stimulation leads 20 and/or lead extension 24.

Electrical stimulation is provided by the IPGs 18 to the electrode arrays 22 in accordance with a set of stimulation parameters. Such stimulation parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 18 supplies constant current or constant voltage to the electrode array 22), pulse duration (measured in microseconds), and pulse frequency (measured in pulses per second, or Hertz). Electrical stimulation of the tissue will occur between two (or more) electrodes, one of which may be the case of the IPG 18, a patch electrode, or the like. While all of the IPGs 18 operate to apply stimulation energy to the tissue in accordance with a stimulation parameter set, each of the IPGs 18 delivers the stimulation energy in a different manner.

For example, the first IPG 18(1) (shown in FIG. 2) may take the form of an IPG capable of independently delivering constant current to the electrodes of the array 22 over multiple channels in either a multipolar or monopolar manner. The second IPG 18(2)(shown in FIG. 2) may take the form of an IPG capable of delivering constant current to the electrodes of the array 22 over only a single channel in only a monopolar manner. The third IPG 18(3)(shown in FIG. 3) may take the form of an IPG capable of uniformly delivering constant voltage over multiple channels in either a multipolar or monopolar manner. Notably, the types of IPGs are not limited to the foregoing described IPGs 18. For example, an IPG may be capable of uniformly delivering constant current over multiple channels or a single channel in either a multipolar or monopolar manner.

Figure 4:
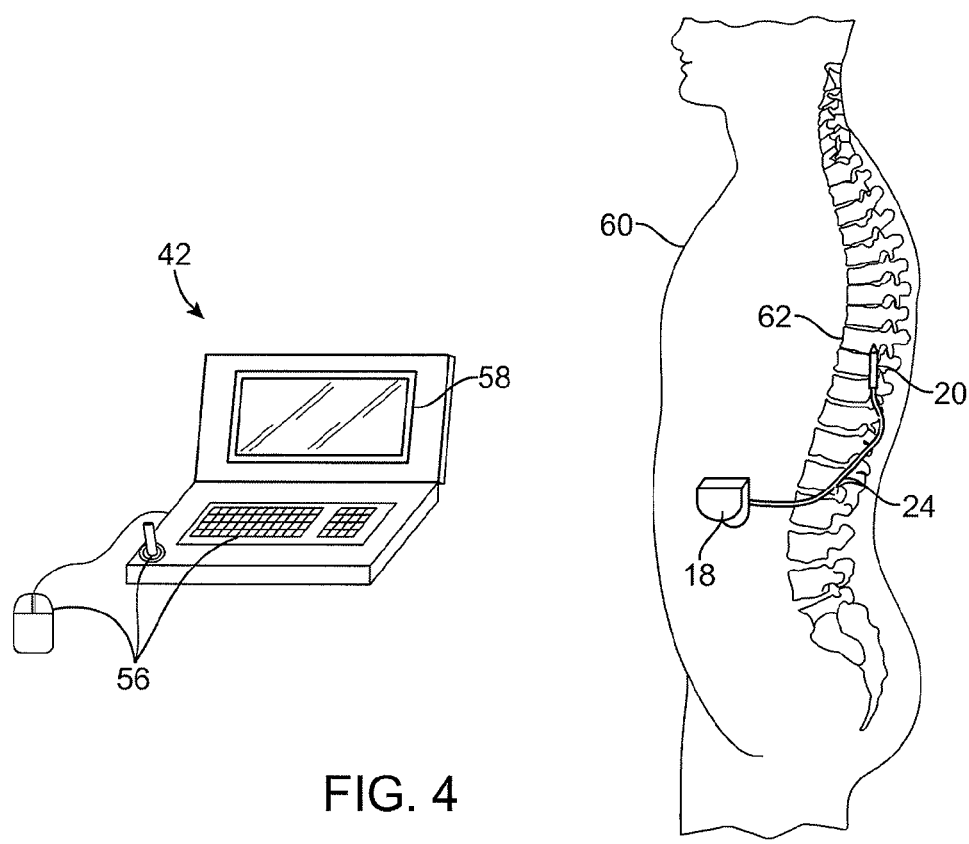
FIG. 4 is a plan view of the Clinician Programmer System (CPS) and the implantable SCS device of FIG. 1 in use with a patient.

As shown in FIG. 4, the implantable components 12 (which includes one of the IPGs 18, the stimulation lead(s) 20, and if needed, the lead extension(s) 24 and adapter(s) 26) may be implanted within a patient 60 using the surgical components 16, which include an insertion tool, such as a hollow needle 28, a guidewire or stylet 30, and tunneling tools 32 (shown in FIG. 1). The stimulation lead(s) 20 may be percutaneously implanted within the spinal column 62 of the patient 60 through the use of the needle 28 and the stylet 30. The preferred placement of the stimulation leads 20 is such that the electrode array 22 is adjacent (i.e., resting upon) the dura nearest the target area of the spinal cord to be stimulated. For example, the needle 28 with stylet 30 is inserted through the back into the epidural space of the patient. The stylet 30 is then removed from the needle 28 to create a hollow opening, and a syringe (not shown) is inserted in the needle 28 to inject saline (3-5 cc) to ensure the needle tip has entered the epidural space. One of the stimulation leads 20 is then passed through the needle 28 into the epidural space. The other stimulation lead 20 is introduced into the epidural space in the same manner. After the stimulation leads 20 are placed, the needle 28 is then pulled out, and an anchor (not shown) is placed around the stimulation leads 20 at the exit site and sutured in place to prevent movement of the stimulation leads 20.

Due to the lack of space near the location where the stimulation leads 20 exit the spinal column 62, the selected IPG 18 is generally implanted in a surgically-made pocket either in the abdomen or above the buttocks. The IPG 18 may, of course, also be implanted in other locations of the patient's body. The lead extension(s) 24 facilitate locating the IPG 18 away from the exit point of the electrode lead(s) 20, and the adapter(s) 26 facilitate mating of the IPG 18, which may otherwise be incompatible with the lead extension(s) 24 and stimulation lead(s) 20, to the lead extension(s) 24. The lead extension(s) 24, for example, may be tunneled from the implantation site of the IPG 18 up to the spinal column 62 using the tunneling tools 32.

Referring still to FIGS. 1 and 2, the external components 14 may include an external trial stimulator (ETS) 34, an external charger 36, a charging port 38, a plurality of different hand-held programmers (HHPs) 40 respectively associated with the different IPGs 18, a clinicians programmer station (CPS) 42, percutaneous lead extension(s) 44 (if needed), external cable(s) 46, and one or more adapters 48 (if needed).

The ETS 34 is capable of being used on a trial basis for a period of time (e.g., 7-14 days) after the stimulation lead(s) 20 have been implanted, and prior to implantation of the IPG 18, to test the effectiveness of the stimulation that is to be provided. The stimulation lead(s) 20 may be connected to the ETS 34 (via one or more connectors on the ETS 34) through the use of the lead extension(s) 44 and external cable(s) 46. Notably, the specific stimulation lead(s) 20 implanted within the patient are typically designed to mate with a specific one of the IPGs 18. As such, the ETS 34 will generally be designed to directly mate with a specific type of stimulation lead. Thus, if specific stimulation lead(s) 20 implanted within the patient are not compatible with the ETS 34, the adapter(s) 48 can be used to connect the ETS 34 to the stimulation lead(s) 20, lead extension(s) 44, or external cable(s) 46. Alternatively, the ETS 34 may have separate dedicated ports (not shown) capable of respectively mating with different stimulation leads and associates lead extensions and external cables. As will be described in further detail below, the ETS 34 may optionally be configured for delivering lesion-forming electrical energy in the form of radio frequency (RF) current to the stimulation leads 20, or an existing RF generator may be used for that purpose.

When needed, an external charger 36 is non-invasively coupled with the IPG 18 through a communications link 50, e.g., an inductive link, allowing energy stored or otherwise made available to the charger 36 via the charging port 38 to be coupled into a rechargeable battery housed within the IPG 18. The HHP 40 may be used to control the IPG 18 via a suitable non-invasive communications link 52, e.g., an RF link. Such control allows the IPG 18 to be turned on or off, and generally allows stimulation parameters to be set within prescribed limits. The HHP 40 may also be linked with the ETS 34 through another communications link 54, e.g., an RF link, to likewise set stimulation parameters within prescribed limits. Thus, the HHP 40 is considered to be in "telecommunicative" contact with the IPG 18 or ETS 34.

Modifying the stimulation parameters in the programmable memory of the IPG 14 after implantation (or in the ETS 34) may be performed by a physician or clinician using the CPS 42, which can directly communicate with the IPG 18 or indirectly communicate with the IPG 18 via the HHP 40. That is, the CPS 42 can be used by the physician or clinician to modify parameters of the stimulation pulses delivered by electrode array 22 near the spinal cord. In the illustrated embodiment, the CPS 42 is linked to the HHP 40 via another communications link 56, e.g., an infra red link. Alternatively, the CPS 42 can be coupled directly to the ETS 34 via a communications link (not shown) or cable. Thus, the CPS 42 is considered to be in "telecommunicative" contact with the IPG 18 or ETS 34. As will be described in further detail below, the CPS 42 may optionally be capable of programming a drug pump or ablation system (shown in FIG. 2) via link 53.

The overall appearance of the CPS 42 is that of a laptop personal computer (PC). Thus, in this embodiment illustrated in FIG. 4, the CPS 42 includes a user input device 56 (e.g., a keyboard, joystick, and a mouse) and a display (e.g., monitor, LED array, or the like) 58 housed in a case. Thus, the programming methodologies can be performed by executing software instructions contained within the CPS 42. Alternatively, such programming methodologies can be performed using firmware or hardware. In any event, the CPS 18 may actively control the characteristics of the electrical stimulation generated by the IPG 18 (or ETS 34) to allow the optimum stimulation parameters to be determined based on patient feedback and for subsequently programming the IPG 18 (or ETS 34) with the optimum stimulation parameters.

Significantly, the ETS 34, under control of the CPS 42, or alternatively under direct control without the CPS 42, is capable of emulating all three of the IPGs 18 by respectively operating in three stimulation energy delivery modes. The programming software package installed in the CPS 42 allows the physician to test/trial all of the IPGs 18 while the stimulation leads 20 remain in place, without the need to switch software platforms or the IPGs 18. For example, the patient can determine whether he or she wants a smaller IPG with streamlined functionality, such as the IPG 18(2), or a more functionality complex IPG (which has the benefit of more stimulation options, yet is larger in size), such as either of the IPGs 18(1) and 18(3), with the IPG 18(1) providing the benefit of allowing fractionalized stimulation to the electrodes. Also, the patient has the ability to feel the improvement of therapy between IPGs manufactured by different competitors. This is especially useful when a patient has decided to replace their currently implanted IPG. This capability allows the surgeon and patient to determine in the operating room the most optimal IPG for permanent implant based on patient feedback in a time-efficient manner, thereby saving valuable time in the operating room, reducing both procedure time and risk.

The stimulation energy delivery modes in which the ETS 34 can be operated differ from each other in at least one aspect of stimulation. For example, in one mode, the ETS 34 may be operated to deliver the stimulation energy at a constant current to the electrodes, and in another mode, the ETS 34 may be operated to deliver the stimulation energy at a constant voltage to the electrodes. For the purposes of this specification, stimulation energy is delivered at a constant current if it is maintained at a constant current amplitude (e.g., 5 mA) when the electrode impedance varies, and stimulation energy is delivered at a constant voltage if it is maintained at a constant voltage amplitude (e.g., 5V) even when the electrode impedance varies.

As another example, in one mode, the ETS 34 may be operated to independently deliver the stimulation energy to the active electrodes, and in another mode, the ETS 34 may be operated to uniformly deliver the same stimulation energy to the active electrodes. For the purposes of this specification, stimulation energy is independently delivered to the electrodes if it is simultaneously delivered to the respective electrodes at different magnitudes. For example, stimulation energy having a current magnitude of 3 mA and 5 mA can be simultaneously delivered to electrodes E4 and E5 on the first stimulation lead 20(1). For the purposes of this specification, the stimulation energy is uniformly delivered to the electrodes if it is simultaneously delivered to the respective electrodes at the same magnitude. For example, stimulation energy at 3V is delivered to each of electrodes E4 and E5 on the first stimulation lead 20(1), or stimulation energy at 5V is delivered to each of electrodes E4 and E5 on the first stimulation lead 20(1).

As still another example, in one mode, the ETS 34 may be operated to deliver the stimulation energy to the electrodes over multiple channels, and in another mode, the ETS 34 may be operated to deliver the stimulation energy to the electrodes only over a single channel. For the purposes of this specification, stimulation energy is delivered to the electrodes over multiple channels if it is delivered to the electrodes in accordance with multiple stimulation parameter sets. For example, electrical pulse parameters can be assigned to different combinations of electrodes to create four channels that are combined into a single program, as follows: Channel 1 (E1: −4 mA, 60 pps, 300 µs; E3: +4 mA, 60 pps, 300 µs); Channel 2 (E6: −4 mA, 50 pps, 300 µs; E7: −2 mA, 50 pps, 300 µs; E8: +6 mA, 60 pps, 300 µs); Channel 3 (E8: −5 mA, 60 pps, 400 µs; E10: +5 mA, 60 pps, 400 µs); and Channel 4 (E13: −4 mA, 60 pps, 300 µs; E14: +4 mA, 60 pps, 300 µs). In a multichannel device, each of these four channels can be assigned its own unique stimulation parameters. For the purposes of this specification, stimulation energy is delivered to the electrodes over a single channel if it is delivered to the electrodes in accordance with only one stimulation parameter set.

As yet another example, in one mode, the ETS 34 may be operated to deliver the stimulation energy to the electrodes in a monopolar manner, and in another mode, the ETS 34 may be operated to deliver the stimulation energy to the electrodes in a multipolar (e.g., bipolar, tripolar, etc.) manner. For the purposes of this specification, stimulation energy is delivered to the electrodes in a monopolar manner when one or more lead electrodes is activated along with an indifferent electrode, such as the case of the IPG, a patch electrode, or the like, so that stimulation energy is transmitted between the selected lead electrode(s) and the indifferent electrode. For example, electrode E4 on the first stimulation lead 20(1) may be activated as a cathode at the same time that the case is activated as an anode.

For the purposes of this specification, stimulation energy is delivered to the electrodes in a multipolar manner when two or more lead electrodes are activated as anode and a cathode (i.e., one or more of the lead electrodes is activated as an anode and one or more lead electrodes is activated as a cathode), so that stimulation energy is transmitted between the selected lead electrodes. For example, in a bipolar manner, electrode E3 on the first stimulation lead 20(1) may be activated as an anode at the same time that electrode E11 on the second stimulation lead 20(2) is activated as a cathode. In a tripolar manner, electrodes E4 and E5 on the first stimulation lead 20(1) may be activated as anodes at the same time that electrode E12 on the second stimulation lead 20(1) is activated as a cathode. In some embodiments, stimulation energy may technically be delivered to the electrodes in a multipolar manner to emulate monopolar stimulation by activating one or more of the lead electrodes as a cathode and a relatively remote electrode or electrodes as anodes. For example, electrode E7 on the first stimulation lead 20(1) may be activated as a cathode at the same time that electrodes E1 and E2 on the first stimulation lead 20(1) and electrodes E9 and E10 on the second stimulation lead 20(2) are activated as anodes.

Thus, based on the foregoing, the ETS 34 can (1) emulate the IPG 18(1) by being operated in a mode that independently delivers stimulation energy to the electrodes at a constant current over multiple channels in either a multipolar or monopolar manner; (2) emulate the IPG 18(2) by being operated in a mode that uniformly delivers stimulation energy to the electrodes at a constant current over a single channel in a monopolar manner; and (3) emulate the IPG 18(3) by being operated in a mode to uniformly delivery stimulation energy to the electrodes at a constant voltage over multiple channels in either a multipolar or monopolar manner. It should be noted that particular advantages can be provided by having an ETS that is capable of emulating different stimulation energy delivery modes (due to different types of implantable pulse generators on the market), an IPG may be designed that can be operated in different stimulation energy delivery modes. Such an IPG would function, operate, and communicate with external devices in the same manner described herein with respect to the ETS 34.

Figure 5:
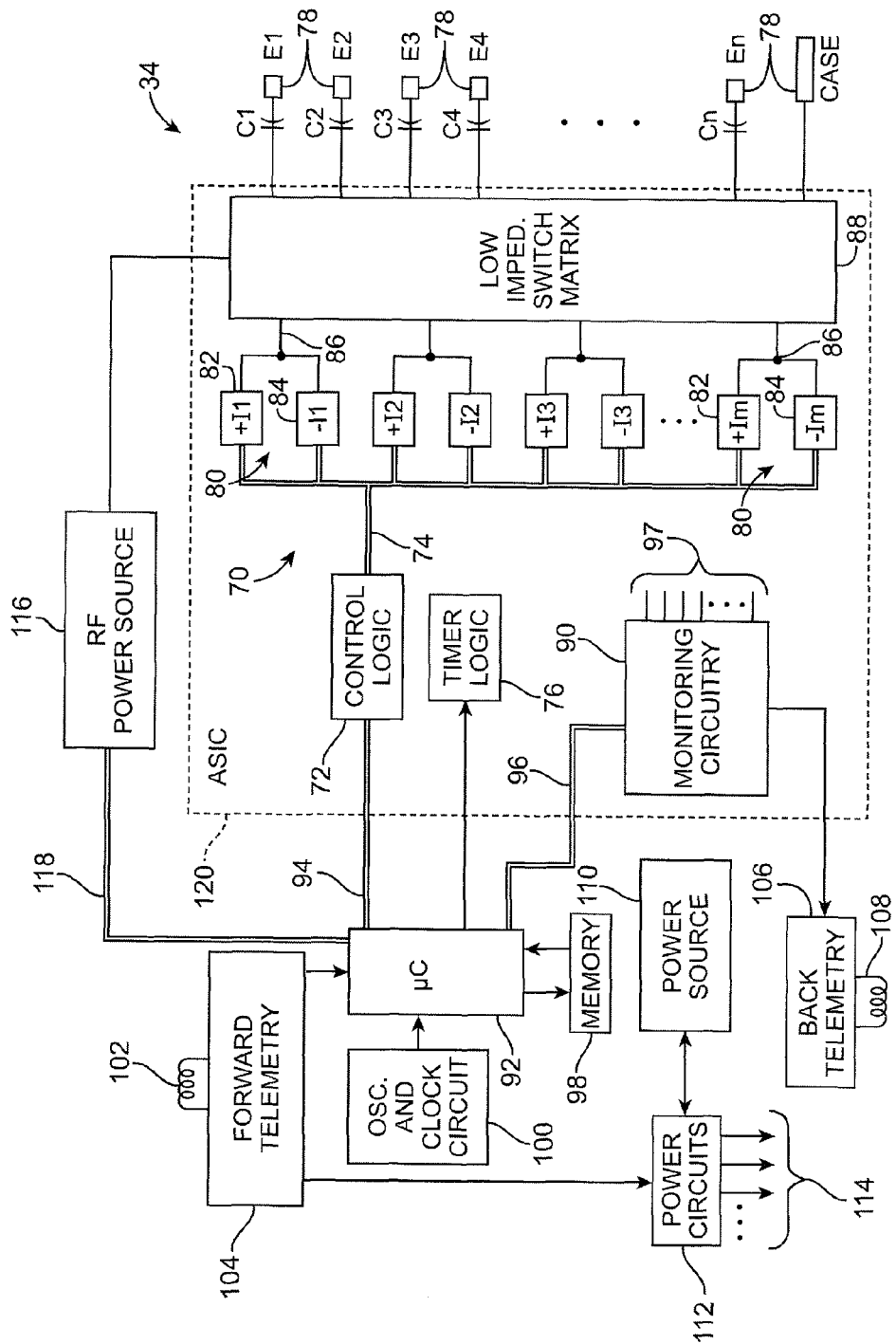
FIG. 5 is a block diagram of an exemplary external trial stimulator (ETS) and/or IPG that may be included in the SCS kit of FIG. 1.

Turning now to FIG. 5, the components of an exemplary embodiment of the ETS 34 (and alternatively an IPG with similar functionality) will now be described. The ETS 34 includes stimulation output circuitry 70 capable of generating electrical stimulation pulses under control of control logic 72 over data bus 74. The duration of the electrical stimulation (i.e., the width of the stimulation pulses), is controlled by timer logic circuitry 76. These stimulation pulses are supplied via capacitors C1-C16 to electrical terminals 78 corresponding to electrodes E1-E16 and the case electrode In the illustrated embodiment, the stimulation output circuitry 70 comprises a plurality m independent current source pairs 80 capable of supplying stimulation energy to the electrical terminals 78 at a specified and known amperage. One current source 82 of each pair 80 functions as a positive (+) current source, while the other current source 84 of each pair 80 functions as a negative (−) current source. The outputs of the positive current source 82 and the negative current source 84 of each pair 80 are connected to a common node 86. The stimulation output circuitry 70 further comprises a low impedance switching matrix 88 through which the common node 86 of each current source pair 80 is connected to any of the electrical terminals 78 via the capacitors C1-C16.

Thus, for example, it is possible to program the first positive current source 82 (+I1) to produce a pulse of +4 mA (at a specified rate and for a specified duration), and to synchronously program the second negative current source 84 (−I2) to similarly produce a pulse of −4 mA (at the same rate and pulse width), and then connect the node 86 of the positive current source 82 (+I1) to the electrical terminal 78 corresponding to electrode E3 and the node 80 of the negative current source 84 (−I2) to the electrical terminal 78 corresponding to electrode E1.

Hence, it is seen that each of the n programmable electrical terminals 78 can be programmed to have a positive (sourcing current), a negative (sinking current), or off (no current) polarity. Further, the amplitude of the current pulse being sourced or sunk from a given electrical terminal 78 may be programmed to one of several discrete levels. In one embodiment, the current through each electrical terminal 78 can be individually set from 0 to ±10 mA in steps of 0.1 mA, within the output voltage/current requirements of the ETS 34. Additionally, in one embodiment, the total current output by a group of electrical terminals 78 can be up to ±20 mA (distributed among the electrodes included in the group). Moreover, it is seen that each of the n electrical terminals 78 can operate in a multipolar mode, e.g., where two or more electrical terminals are grouped to source/sink current at the same time. Alternatively, each of the n electrical terminals 78 can operate in a monopolar mode where, e.g., the electrical terminals 78 are configured as cathodes (negative), and the case of the IPG 18 (or other indifferent electrode) is configured as an anode (positive). It can be appreciated that an electrical terminal 78 may be assigned an amplitude and may be included with any of up to k possible groups, where k is an integer corresponding to the number of channels, and in some embodiments is equal to 4, and with each channel k having a defined pulse width, pulse frequency, and other stimulation parameters. Other channels may be realized in a similar manner. Thus, each channel identifies which electrical terminals 78 (and thus electrodes) are selected to synchronously source or sink current, the pulse amplitude at each of these electrical terminals, and the pulse width and pulse frequency.

In an alternative embodiment, rather than using independently controlled current sources, independently controlled voltage sources for providing stimulation pulses of a specified and known voltage at the electrical terminals 78 can be provided. The operation of this output stimulation circuitry (with respect to IPGs but just as applicable for ETSs), including alternative embodiments of suitable output circuitry for performing the same function of generating stimulation pulses of a prescribed amplitude and width, is described more fully in U.S. Pat. No. 6,993,384, which is expressly incorporated herein by reference.

The ETS 34 further comprises monitoring circuitry 90 for monitoring the status of various nodes or other points 91 throughout the ETS 34, e.g., power supply voltages, temperature, battery voltage, and the like. The monitoring circuitry 90 is also configured for measuring voltage values at the electrical terminals 78, which as will be described in further detail below, can be used to output constant voltage at the electrical terminals 78 during certain operational modes despite the fact that constant current sources 80 are used to supply stimulation energy. In the alternative case where constant voltage sources are used to supply stimulation energy to the electrical terminals 78, the monitoring circuitry 90 can be configured to measure current values at the electrical terminals 78, which can be used to output constant current at the electrical terminals 78 during certain operational modes.

The ETS 34 further comprises processing circuitry in the form of a microcontroller (μC) 92 that controls the control logic over data bus 94, and obtains status data from the monitoring circuitry 90 via data bus 96. The μC 92 additionally controls the timer logic 78. The ETS 34 further comprises memory 98 and oscillator and clock circuit 100 coupled to the μC 92. The μC 92, in combination with the memory 98 and oscillator and clock circuit 100, thus comprise a microprocessor system that carries out a program function in accordance with a suitable program stored in the memory 98. Alternatively, for some applications, the function provided by the microprocessor system may be carried out by a suitable state machine.

Thus, the μC 92 generates the necessary control and status signals, which allow the μC 92 to control the operation of the ETS 34 in accordance with a selected operating program and stimulation parameters. In controlling the operation of the ETS 34, the μC 92 is able to individually generate stimulus pulses at the electrical terminals 78 using the output stimulation circuitry 70, in combination with the control logic 72 and timer logic 76, thereby allowing each electrical terminal 78 (and thus each electrode) to be paired or grouped with other electrical terminals 78 and thus other electrodes), including the monopolar case electrode, to control the polarity, amplitude, rate, pulse width and channel through which the current stimulus pulses are provided. The μC 92 facilitates the storage of electrical parameter data measured by the monitoring circuitry 90 within memory 98, and also provides any computational capability needed to analyze such electrical parameter data.

For example, if the mode in which the ETS 34 is currently operated requires a constant voltage output, the μC 92 actively maintains this constant voltage output at the electrical terminals 78. Notably, absent such active control, the voltage output will vary in response to electrode impedance changes (often caused by changes in tissue conductivity, tissue growth or lead migration) as a natural consequence of the current sources 80 maintaining a constant current output in response to such electrode impedance changes. To compensate for this, the μC 92 automatically varies the current output by the current sources 80 to maintain the desired constant voltage output. For example, as the electrode voltage, as measured by the monitoring circuitry 90, increases in response to a decrease in electrode impedance, the μC 92 will immediately decrease the current output by the current sources 80 to maintain the desired voltage output. As the electrode voltage, as measured by the monitoring circuitry 90, decreases in response to an increase in electrode impedance, the μC 92 will immediately increase the current output by the current sources 80 to maintain the desired voltage output.

In the alternative case where voltage sources are used in the stimulation output circuitry 70 instead of current sources, if the mode in which the ETS 34 is currently operated requires a constant current output, the μC 92 actively maintains this constant current output at the electrical terminals 78. Notably, absent such active control, the current output will vary in response to electrode impedance changes as a natural consequence of the voltage sources maintaining a constant voltage output in response to such electrode impedance changes. To compensate for this, the μC 92 automatically varies the voltage output by the voltage sources to maintain the desired constant current output. For example, as the electrode current, as measured by the monitoring circuitry 90, increases in response to a decrease in electrode impedance, the μC 92 will immediately decrease the voltage output by the voltage sources to maintain the desired current output. As the electrode current, as measured by the monitoring circuitry 90, decreases in response to an increase in electrode impedance, the μC 92 will immediately increase the voltage output by the voltage sources to maintain the desired current output.

The ETS 34 further comprises an alternating current (AC) receiving coil 102 for receiving programming data (e.g., the operating program and/or stimulation parameters) from the CPS 42 via the HHP 40 (or directly, either wirelessly or via a cable) in an appropriate modulated carrier signal, and forward telemetry circuitry 104 for demodulating the carrier signal it receives through the AC receiving coil 102 to recover the programming data, which programming data is then stored within the memory 98, or within other memory elements (not shown) distributed throughout the ETS 34.

The ETS 34 further comprises back telemetry circuitry 106 and an alternating current (AC) transmission coil 108 for sending informational data sensed through the monitoring circuitry 90 to the CPS 42 (or directly, either wirelessly or via a cable). The back telemetry features of the ETS 34 also allow its status to be checked. For example, any changes made to the stimulus parameters are confirmed through back telemetry, thereby assuring that such changes have been correctly received and implemented within the ETS 34. Moreover, upon interrogation by the CPS 42, all programmable settings stored within the ETS 34 may be uploaded to the CPS 42.

The ETS 34 further comprises a power source 110 (e.g., a battery) and power circuits 112 for providing the operating power to the ETS 34. The battery 104 provides an unregulated voltage to the power circuits 112. The power circuits 112, in turn, generate the various voltages 114, some of which are regulated and some of which are not, as needed by the various circuits located within the ETS 34.

In an optional embodiment, the ETS 34 comprises a tissue ablation source, and in the illustrated embodiment, a radio frequency (RF) source 116, coupled to the electrical terminals 78 via the switch matrix 88. The μC 92 controls the delivery of RF ablation energy from the RF source 116 via bus 118, while also controlling the switch matrix 88 in a manner that delivers the ablation energy to the desired electrical terminals 78. This capability allows a physician to lesion target tissues using the same leads 20 if the stimulation trial is unsuccessful. Ablation energy can be delivered in a multipolar manner or in a monopolar manner (e.g., by using an external ground pad).

While the invention has been described in the context of an SCS system, lesioning is especially likely to be therapeutic in the brain; for instance, in patients with Parkinson's disease or epilepsy. Additional conditions that could benefit from lesioning techniques include chronic pain, occipital neuralgia, phantom limb pain, radiation plexopathy, and postherpetic neuralgia, among others.

As shown in FIG. 5, much of the circuitry included within the ETS 34 may be realized on a single application specific integrated circuit (ASIC) 120. This allows the overall size of the ETS 34 to be quite small, and readily housed within a portable case that can be conveniently worn by the patient. Alternatively, most of the circuitry included within the ETS 34 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the ETS 34, including providing power regulation, stimulus output, impedance measurement and monitoring. A digital IC (DigIC) may be provided to function as the primary interface between the processor IC and analog IC by controlling and changing the stimulus levels and sequences of the current output by the stimulation circuitry in the analog IC when prompted by the processor IC.

It should be noted that the diagram of FIG. 5 is functional only, and is not intended to be limiting. Those of skill in the art, given the descriptions presented herein, should be able to readily fashion numerous types of electrical stimulation circuits, or equivalent circuits, that carry out the functions indicated and described, which functions include producing a stimulus current or voltage on selected groups of electrodes.

Figures 1, 6:
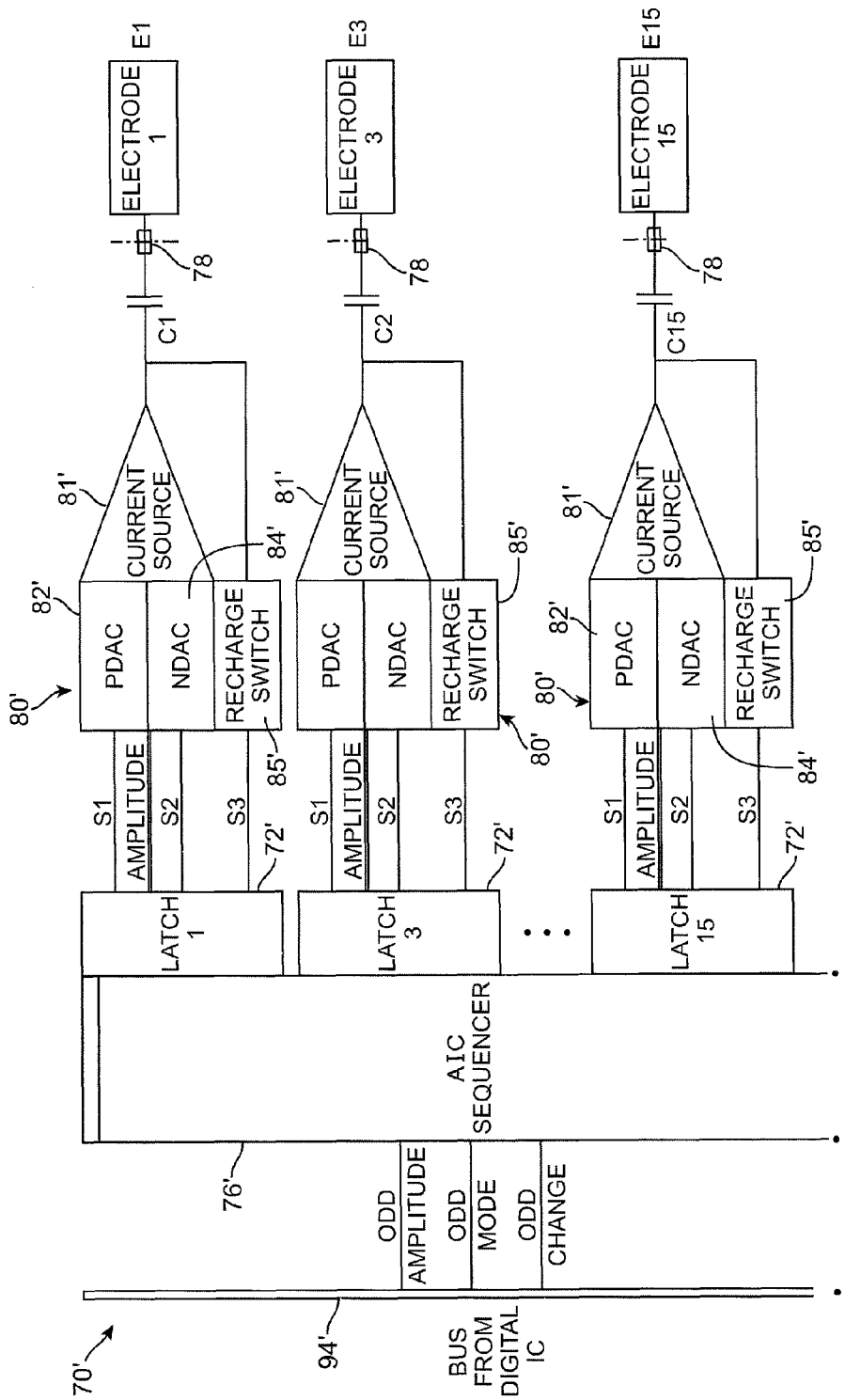
FIG. 6 is a block diagram is an alternative embodiment of stimulation output circuitry that can be used in the external trial stimulator (ETS) of FIG. 5.
Figures 2, 6:
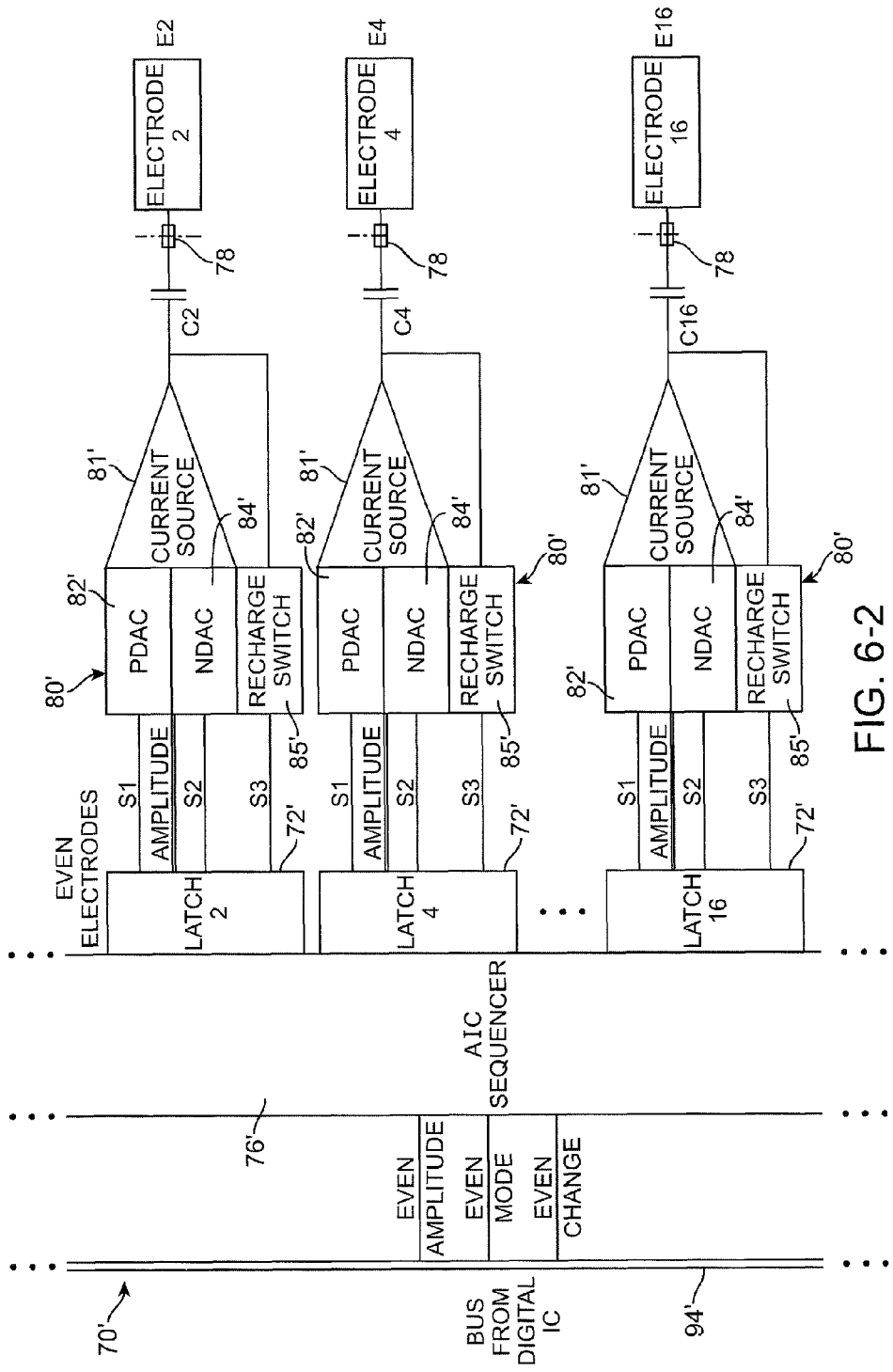
Figures 3, 6:
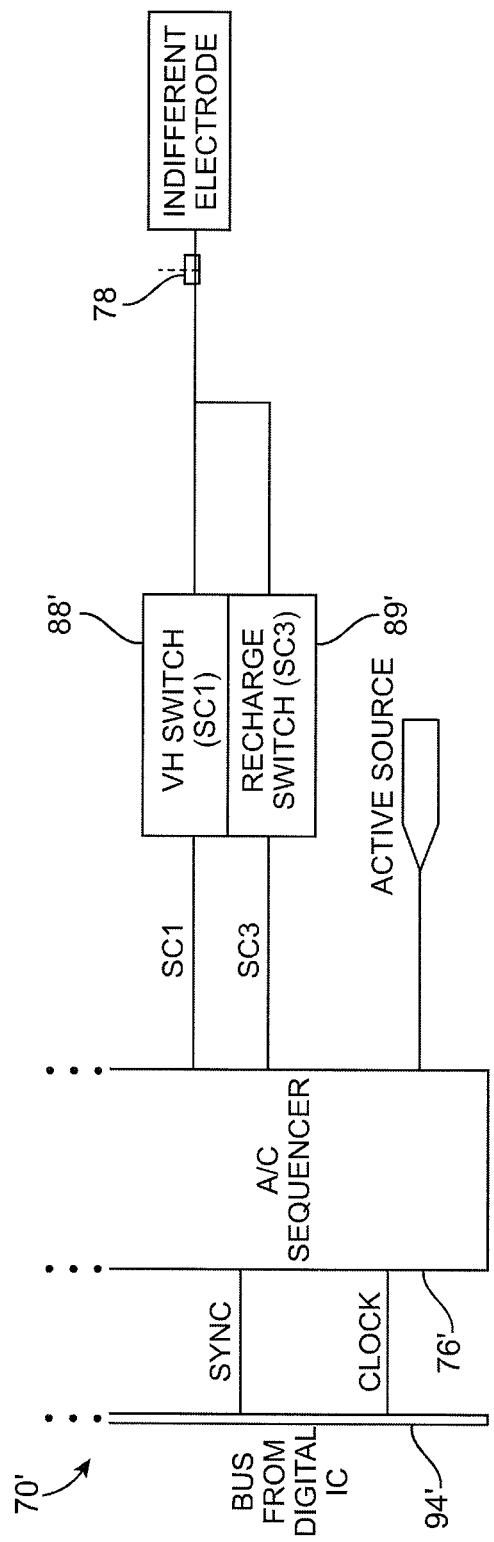

For example, an alternative embodiment of stimulation output circuitry 70' illustrated in FIG. 6 does not include a low impedance switching matrix 88, but rather includes a bi-directional current source 80' for each of the electrical terminals 78. Each of the bi-directional current sources 80' includes a current source 81', a positive digital-to-analog converter (PDAC) 82' that causes the current source 81' to source electrical current, a negative digital-to-analog converter (NDAC) 84' that causes the current source 81' to sink electrical current, and a recharge circuit 85'.

Control circuitry that includes an analog integrated circuit (AIC) sequencer circuit 76' receives control data from a digital integrated circuit (IC) (not shown) over bus 94'. Such data includes odd and even amplitude data, where "odd" and "even" refer to the electrode number (with electrodes E1, E3, E5, etc. being "odd" electrodes; and electrodes E2, E4, E6, etc. being "even" electrodes). The control circuitry also includes latch circuits 72' that are connected to the AIC sequencer 76', with the number of latch circuits 72' equal to the number of electrodes E1-E16.

Each latch circuit 72' includes an amplitude bus on which the amplitude data is placed, an S1 line for designating a positive amplitude, an S2 line for designating a negative amplitude, and an S3 line for designating a recharge state. Thus, the PDAC 82' is enabled by a signal on the S1 line when a current having the amplitude specified on the amplitude bus is to be sourced from the current source 81' to the electrical terminal 78 via a respective capacitor Cn; the PDAC 82' is enabled by a signal on the S2 line when a current having the amplitude specified on the amplitude bus is to be sunk into the current source 81' from the electrical terminal 78 via a respective capacitor Cn; and the recharge circuit 85' is enabled by a signal on the S3 line when it is desired to remove charge from the respective capacitor Cn. The control circuitry also includes a switch 88' that allows an indifferent electrode, such as the case of the IPG, to be turned on upon receipt of a signal on an SC1 line coupled to the AIC sequencer 76'. Similarly, the control circuitry also includes a switch 89' that allows the indifferent electrode to be selectively connected to ground or another source upon receipt of a signal on an SC3 line coupled to the AIC sequencer 72'.

It should be noted that rather than emulating IPGs, the ETS 34 may alternatively emulate receiver-stimulators (not shown) that can be mated to the stimulation leads 20. In this case, the power source, e.g., a battery, for powering the receiver, as well as control circuitry to command each of the receiver-stimulators, will be contained in an external controller inductively coupled to the respective receiver-stimulator via an electromagnetic link. For example, such control circuitry can be contained in the CPS 42 and/or HHP 40 or other external device. Data/power signals would be transcutaneously coupled from a transmission coil placed over the respective receiver-stimulator. The implanted receiver-stimulator receives the signal and generates the stimulation in accordance with the control signals.

As briefly discussed above, the CPS 42, when needed, is capable of operating the ETS 34 in one of three different stimulation energy delivery modes; that is, a first stimulation energy delivery mode that emulates the first IPG 18(1), a second stimulation energy delivery mode that emulates the second IPG 18(2), and a third stimulation energy delivery mode that emulates the third IPG 18(3).

Figure 7:
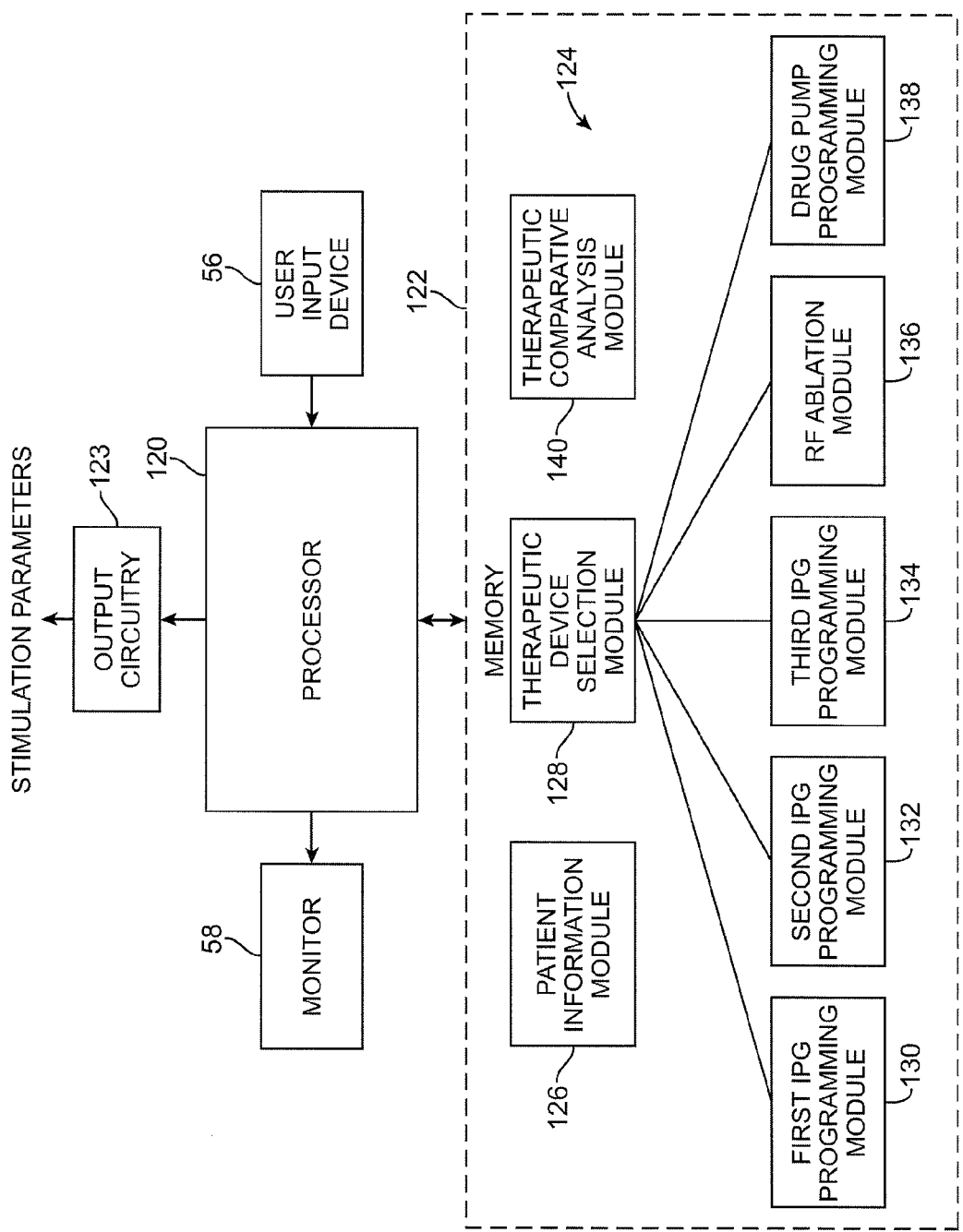
FIG. 7 is a block diagram of the functional components of a Clinicians Programmer Station (CPS) included in the SCS kit of FIG. 1.

Referring to FIG. 7, the functional components of the CPS 42 will now be described. The CPS 42 generally includes a processor 120 (e.g., a central processor unit (CPU)), memory 122 that stores a stimulation programming package(s) 124, which can be executed by the processor 120 to allow a user to selectively test/trial each of the IPGs 18 via the ETS 34 (and optionally, to test drug pumps and/or ablation systems), and output circuitry 123 (e.g., via the telemetry circuitry of the HHP 40) for outputting stimulation parameters to the ETS 34 via the telemetry circuitry of the HHP 40 or directly to the ETS 34. The programming package 124 also allows the user to therapeutically ablate tissue via the ETS 34, and to alternatively test/trial other therapeutic devices, such as drug pumps (not shown). To this end, the IPG programming package 124 includes a patient information module 126, which allows entry of specific patient information and generation of patient reports. The programming package 124 further includes a therapeutic device selection module 128 that allows the user to select between one of the IPGs 18, an RF ablation device, and a drug pump (not shown). The programming package 124 further comprises a first IPG programming module 130, a second IPG programming module 132, a third IPG programming module 134, an RF ablation module 136, and a drug pump programming module 138, all of which are linked to the selection module 128. The programming package 124 also includes a therapeutic comparative analysis module 140, which automates testing/trialing of the different IPGs 18. In the preferred embodiment, the programming package 124 comprises a variety of features that facilitate its interoperability, such as each of switching between modules (e.g., with tabbed screens), auto information transfer, parameter adaptation, running modules concurrently or displayed on one screen, etc.

Referring to FIG. 8, execution of the patient information module 126 provides a patient information screen 142 that allows entry, reviewing, and printing of patient-specific information, such as profile information, clinic information, hardware information, stimulation settings, battery usage, case history, patient notes for various time intervals, last visit, serial number, implant date, physician, etc.

Referring to FIG. 9, execution of the selection module 128 provides a therapeutic device selection screen 144 that provides icons 146-154 that the user may click on to select a therapeutic device to be trialed or used. Thus, clicking on icon 146 opens a first IPG programming screen 156 (shown in FIG. 10), clicking on icon 148 opens a second IPG programming screen 158 (shown in FIG. 11), clicking on icon 150 opens a third IPG programming screen 160 (shown in FIG. 12), clicking on icon 152 pulls up an RF ablation delivery screen 162 (shown in FIG. 13), and clicking on icon 154 pulls up a drug pump programming screen 164 (shown in FIG. 14).

Figure 10:
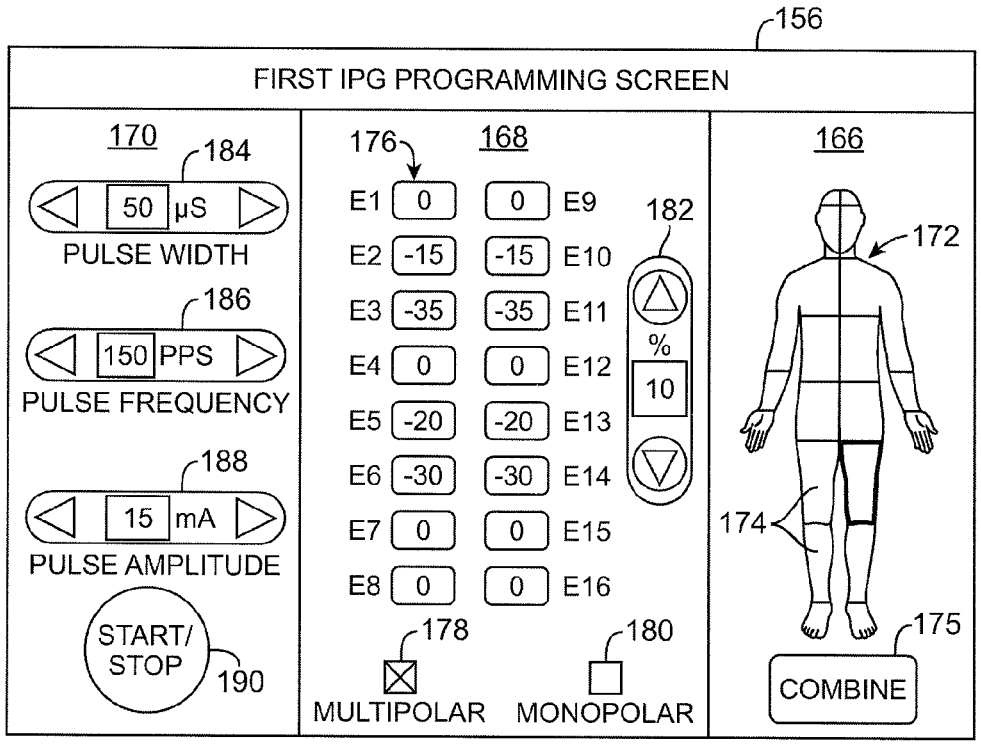
FIG. 10 is an exemplary first IPG programming screen generated by the CPS of FIG. 7.

Referring to FIG. 10, the first IPG programming screen 156 enables different stimulation parameter sets to be transmitted from the CPS 42 to the ETS 34, thereby modifying the stimulation energy output by the ETS 34 to the electrodes 22 in accordance with the first operation mode; in this example, the independent delivery of constant current to the electrodes over multiple channels in a multipolar or monopolar manner. To this end, the programming screen 156 has three exemplary panels 166-170, which allow the user to enter and convey stimulation parameter information to the ETS 34, so that it can be operated in accordance with the first stimulation energy delivery mode.

In this mode, stimulation parameters can be programmed for, e.g., up to four independent paresthesia coverage areas to create a single program. To this end, the first panel 166 provides a graphic of a human body 172 divided into several regions 174. Clicking on one or more of these regions 174 allows the user to determine a set of stimulation parameters for this selected region. In the illustrated embodiment, the right thigh of the patient is highlighted, indicating that this is the region 174 for which stimulation parameters will currently be generated. Clicking on other regions 174 allow the user to likewise determine stimulation parameter sets for these selected regions 174. These stimulation parameter sets can then be combined into a single program by clicking on combination button 175.

The second panel 168 provides a graphic 176 of the electrodes E1-E16 in two columns arranged in accordance with the stimulation leads 20. The second panel 168 includes a multipolar box 178, the clicking of which characterizes the electrodes E1-E16 in a multipolar arrangement, and a monopolar box 180, the clicking of which characterizes the electrodes E1-E16 in a monopolar arrangement.

If a multipolar electrode arrangement is selected, any of the electrodes E1-E16 can be clicked to select the electrode as being either an anode (+), cathode (−), or off (0). In the illustrated embodiment, such selection can be accomplished simply by clicking on the respective electrode multiple times to designate the electrode as a cathode, then an anode, and then off. As shown, electrodes E2, E3, E0, and E11 are designated as cathodes, and electrodes E5, E6, E13, and E14 are designated as anodes. If a monopolar electrode arrangement is selected, any of the electrodes E1-E16 can be clicked to select the electrode as being a cathode (−) or off (0). Such selection can be accomplished simply by clicking on the respective electrode multiple times to toggle designation of the electrode between a cathode and off.

In this embodiment, constant current can be independently provided to the electrodes E1-E16. To this end, the second panel 168 includes an up-down current adjustment control 182, which can be operated to assign a fractionalized current for each of the active electrodes E1-E16. In particular, for each electrode selected to be activated as either a cathode or anode, the user can click on the upper arrow of the control 182 to incrementally increase the absolute value of the fractionalized current of the selected electrode, and the user can click on the lower arrow of the control 182 to incrementally decrease the absolute value of the fractionalized current. Notably, the total fractionalized current value for any group of anodes will equal 100% and the total fractionalized current value for any group of cathodes will equal 100%. As shown, electrodes E2, E3, E10, and E11 have respective fractionalized current values of 15%, 35%, 15%, and 35%, and the electrodes E5, E6, E13, and E14 have respective fractionalized current values of 20%, 30%, 20%, and 30%.

The third panel 170 allows the stimulation energy output by the ETS 34 to be initiated and modified by adjusting each of a pulse width, pulse frequency, and pulse amplitude. To this end, the third panel 170 includes a pulse width adjustment control 184, the right arrow of which can be clicked to incrementally increase the pulse width of the stimulation energy, and the left arrow of which can be clicked to incrementally decrease the pulse width of the stimulation energy. The third panel 170 further includes a pulse frequency adjustment control 186, the right arrow of which can be clicked to incrementally increase the pulse frequency of the stimulation energy, and the left arrow of which can be clicked to incrementally decrease the pulse frequency of the stimulation energy. The third panel 170 further includes a pulse amplitude adjustment control 188, the right arrow of which can be clicked to incrementally increase the pulse amplitude of the stimulation energy, and the left arrow of which can be clicked to incrementally decrease the pulse amplitude of the stimulation energy.

Notably, because the ETS 34 is operated to output the stimulation energy as a constant current, the pulse amplitude will be adjusted in milliamperes. Also, since the fractionalized current between the electrodes E1-E16 is controlled by the fractionalized current adjustment control 182, clicking the pulse amplitude adjustment control 190 globally scales the current through the activated one(s) of the electrodes E1-E16. Adjustment of these stimulation parameters can be accomplished while the stimulation energy is output by the ETS 34 or when no stimulation energy is being output by the ETS 34.

The third panel 170 further includes a stimulation activation/deactivation control 190 that can be clicked to initiate delivery of the stimulation energy and cease delivery of the stimulation energy. Thus, clicking the control 184 to initiate delivery of the stimulation energy will output the stimulation parameters to the ETS 34, which will in turn, apply the stimulation energy to the electrodes in accordance with the stimulation parameters. Manipulation of the previously described controls 182-188 will modify the stimulation parameters transmitted to the ETS 34, which will in turn, modify the characteristics of the stimulation energy applied by the ETS 34 to the electrodes.

In an alternative embodiment, the electrical stimulation parameters, including the pulse width, pulse frequency, and pulse frequency, can be auto-adjusted. To this end, the user may enter beginning and ending values of the pulse width, pulse frequency, and pulse amplitude, and may initiate an automated programming process that gradually adjusts each of these parameters from the beginning value to the end value. In another alternative embodiment, a directional current steering device can be employed, so that the current delivery can be gradually shifted up, down, left, or right amongst the electrodes. Further details discussing current steering interfaces are disclosed in U.S. Pat. No. 6,909,917, which is expressly incorporated herein by reference.

Figure 11:
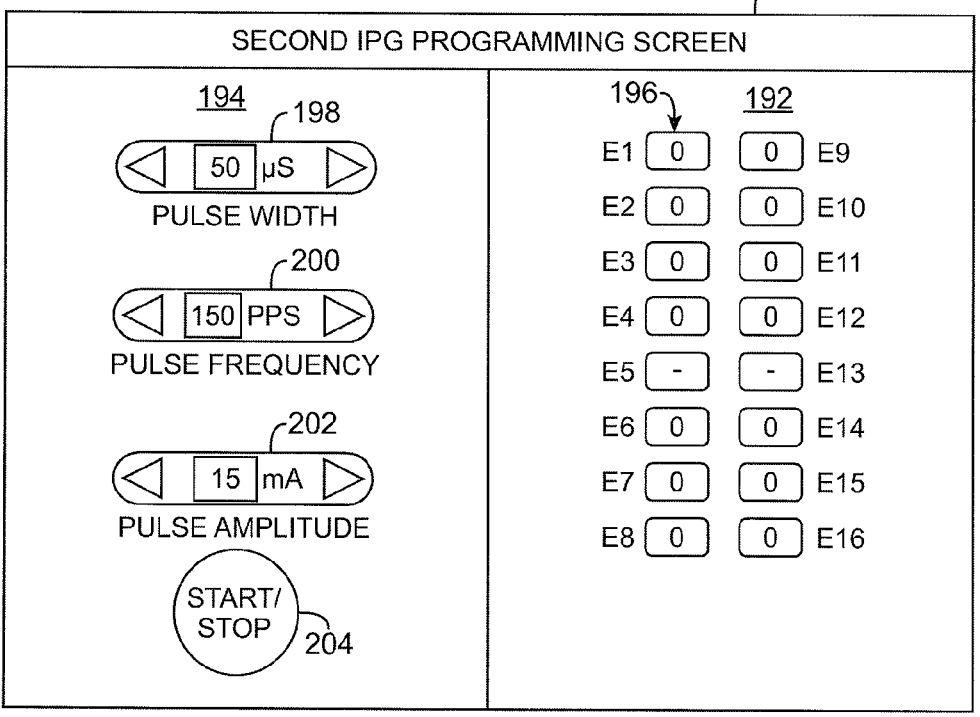
FIG. 11 is an exemplary second IPG programming screen generated by the CPS of FIG. 7.

Referring to FIG. 11, the second IPG programming screen 158 enables different stimulation parameter sets to be transmitted from the CPS 42 to the ETS 34, thereby modifying the stimulation energy output by the ETS 34 to the electrodes 22 in accordance with the second stimulation energy delivery mode; in this example, the uniform delivery of constant current to the electrodes over a single channel in a monopolar manner. To this end, the programming screen 158 may have just two panels 192 and 194, which allow the user to enter and convey stimulation parameter information to the ETS 34, so that it can be operated in accordance with the second stimulation energy delivery mode.

In this example of single-channel mode, no graphic of a human body is shown, since only one paresthesia area is covered by a single program. (In another example, the human body graphic may still be used.) The first panel 192 provides a graphic of the electrodes E1-E16 in two columns arranged in accordance with the stimulation leads 20. The two columns of electrodes E1-E16 can be respectively coupled to two IPGs or may be coupled to a single IPG. Because the ETS 34 only operates in a monopolar manner in the second stimulation energy delivery mode, no control boxes are needed to specify multipolar/monopolar delivery, in contrast to the case in the second panel 168 of the first IPG programming screen 156. In addition, the electrodes E1-E16 can only be clicked to select the electrode as being a cathode (−) or off (0). Such selection can be accomplished simply by clicking on the respective electrode multiple times to toggle designation of the electrode between a cathode and off. As shown, electrodes E5 and E13 have been activated as cathodes. Since stimulation energy is uniformly delivered to the electrodes (i.e., the current is equally distributed amongst the activated ones of the electrodes E1-E16) in this operational mode, no means is provided for individually adjusting the fractionalized current between the electrodes, in contrast to the case with the second panel 168 of the first IPG programming screen 156.

The second panel 194 allows the stimulation energy output by the ETS 34 to be initiated and modified by adjusting each of a pulse width, pulse frequency, and pulse amplitude. To this end, the second panel 194 is identical to the third panel 170 of the first IPG programming screen 156 in that it includes a pulse width adjustment control 198, pulse frequency adjustment control 200, pulse amplitude adjustment control 202, and a stimulation activation/deactivation control 204, which respectively operate in the same manner as the pulse width adjustment control 184, pulse frequency adjustment control 186, pulse amplitude adjustment control 188, and stimulation activation/deactivation control 190 shown in the third panel 170 of the first IPG programming screen 156.

Figure 12:
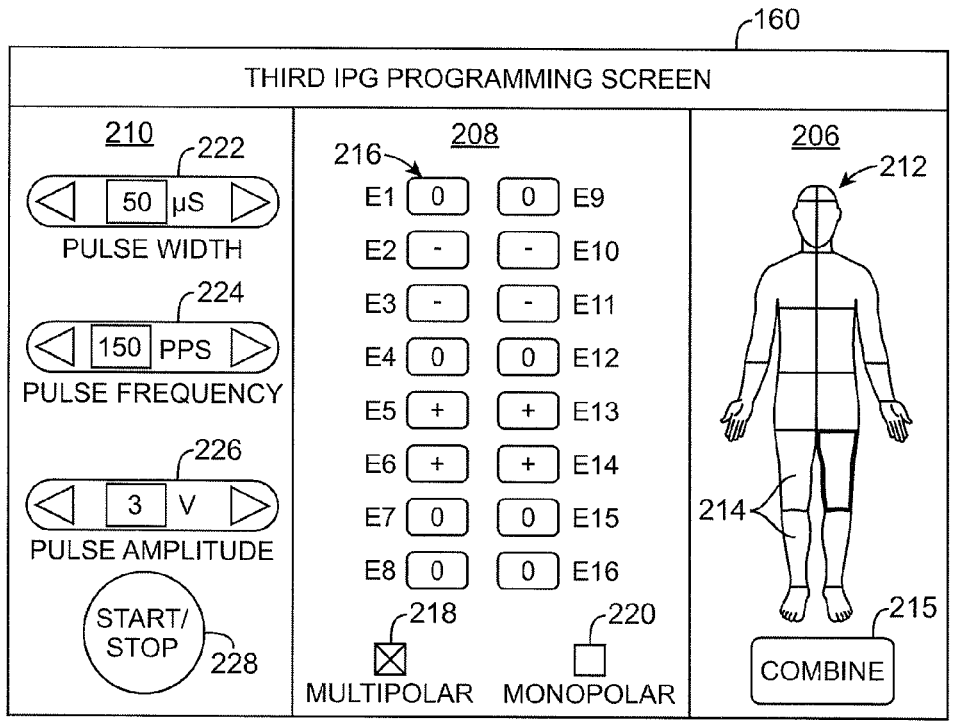
FIG. 12 is an exemplary third IPG programming screen generated by the CPS of FIG. 7.

Referring to FIG. 12, the third IPG programming screen 160 enables different stimulation parameter sets to be transmitted from the CPS 42 to the ETS 34, thereby modifying the stimulation energy output by the ETS 34 to the electrodes E1-E16 in accordance with the third stimulation energy delivery mode; in this example, the uniform delivery of constant voltage to the electrodes over multiple channels in a multipolar or monopolar manner. To this end, the programming screen 160 has three panels 206-210, which allow the user to enter and convey stimulation parameter information to the ETS 34, so that it can be operated in accordance with the third stimulation energy delivery mode.

In this multi-channel mode, stimulation parameters can be programmed for up to four independent paresthesia coverage area to create a single program. To this end, the first panel 206 is identical to the first panel 166 of the first IPG programming screen 156 in that it includes a graphic of a human body 212 divided into several regions 214, and a combination button 215 that operate in the same manner as the graphic 172 and combination button 175 illustrated in the first panel 166 of the first IPG programming screen 156. The second panel 208 provides a graphic 216 of the electrodes E1-E16 in two columns arranged in accordance with the stimulation leads 20. In this operational mode, the electrodes E1-E16 can be operated in either a multipolar manner or a monopolar manner, and thus, include the multipolar box 218 and monopolar box 220 that function in the same manner as the multipolar box 178 and monopolar box 180 illustrated in the second panel 168 of the first IPG programming screen 156.

As discussed above with respect to the second panel 168 of the first IPG programming screen 156, any of the electrodes E1-E16 can be clicked to select the electrode as being either an anode (+), cathode (−), or off (0) in the bipolar electrode arrangement, and any of the electrodes E1-E16 can be clicked to select the electrode as being a cathode (−) or off (0) in the monopolar electrode arrangement. In the illustrated case, electrodes E2, E3, E10, and E11 have been activated as cathodes, and electrodes E5, E6, E13, and E14 have been activated as anodes. Since stimulation energy is uniformly delivered to the electrodes (i.e., the voltage is equally applied to the activated ones of the electrodes E1-E16) in this operational mode, no means is provided for individually adjusting the voltages at the electrodes, in contrast to the case shown in the second panel 168 of the first IPG programming screen 156.

The third panel 210 allows the stimulation energy output by the ETS 34 to be initiated and modified by adjusting each of a pulse width, pulse frequency, and pulse amplitude. To this end, the third panel 210 is identical to the third panel 170 of the first IPG programming screen 156 in that it includes a pulse width adjustment control 222, pulse frequency adjustment control 224, pulse amplitude adjustment control 226, and a stimulation activation/deactivation control 228, which respectively operate in the same manner as the pulse width adjustment control 184, pulse frequency adjustment control 186, pulse amplitude adjustment control 188, and stimulation activation/deactivation control 190 shown in the third panel 170 of the first IPG programming screen 156.

Notably, the types of programming screens are not limited to the foregoing described programming screens. For example, an IPG programming screen may enable different stimulation parameter sets to be transmitted from the CPS 42 to the ETS 34, thereby modifying the stimulation energy output by the ETS 34 to the electrodes E1-E16 in accordance with the fourth stimulation energy delivery mode; for example, the uniform delivery of constant current to the electrodes over multiple channels in a multipolar or monopolar manner.

Figure 13:
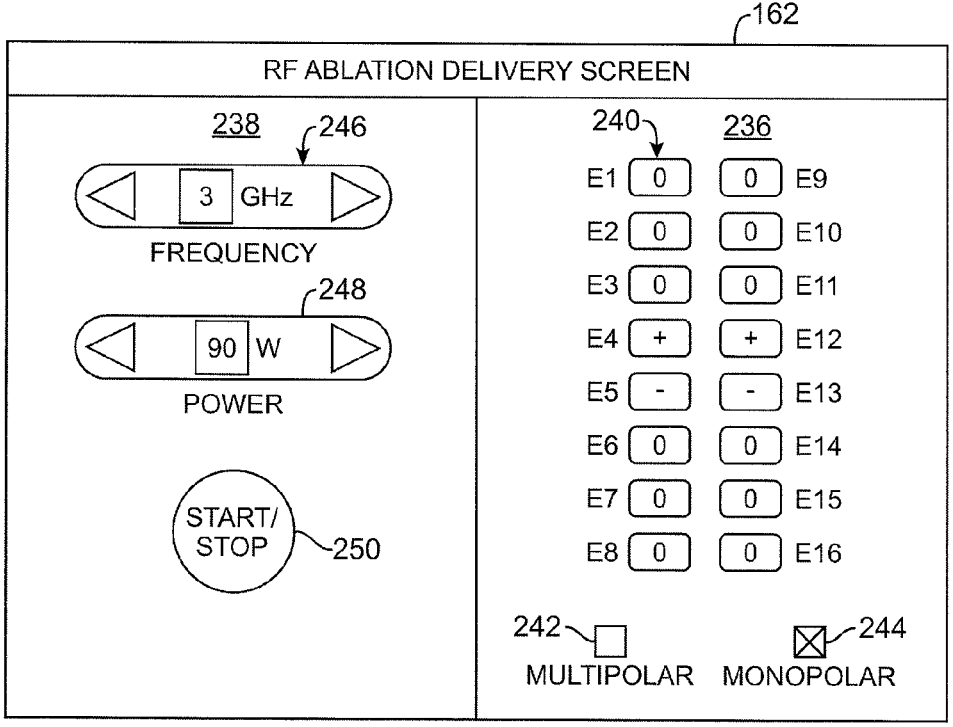
FIG. 13 is an exemplary radio frequency (RF) ablation delivery screen generated by the CPS of FIG. 7.

Referring to FIG. 13, the RF ablation delivery screen 162 enables delivery of RF ablation energy to any the electrodes E1-E16 to treat targeted tissue. To this end, the programming screen 162 has two panels 236 and 238, which allow the user to delivery the ablation energy in a defined manner. The first panel 236 provides a graphic 240 of the electrodes E1-E16 in two columns arranged in accordance with the stimulation leads 20. The first panel 236 includes a multipolar box 242, the clicking of which characterizes the electrodes E1-E16 in a multipolar arrangement, and a monopolar box 244, the clicking of which characterizes the electrodes E1-E16 in a monopolar arrangement. If a multipolar electrode arrangement is selected, any of the electrodes E1-E16 can be clicked to select the electrode as being an electrode of a first polarity (designated with a "+"), an electrode of a second polarity (designed with a "−"), or off (designated with a "0").

In the illustrated embodiment, such selection can be accomplished simply by clicking on the respective electrode multiple times to designate the electrode with a first polarity, then a second polarity, and then off. As shown, electrodes E4 and E12 are designated with the first polarity (+), and electrodes E5 and E13 are designated with the negative polarity (−). If a monopolar electrode arrangement is selected, any of the electrodes E1-E16 can be clicked to select the electrode as having the first polarity (+) or off (0). Such selection can be accomplished simply by clicking on the respective electrode multiple times to toggle designation of the electrode between a cathode and off.

The second panel 238 allows the ablation energy output by the ETS 34 to be initiated and modified by adjusting each of a frequency and power. Optionally, a duty cycle of the ablation energy can be adjusted). To this end, the second panel 238 includes a frequency adjustment control 246, the right arrow of which can be clicked to incrementally increase the frequency of the ablation energy, and the left arrow of which can be clicked to incrementally decrease the frequency of the ablation energy. The second panel 238 further includes a power adjustment control 248, the right arrow of which can be clicked to incrementally increase the power of the ablation energy, and the left arrow of which can be clicked to incrementally decrease the power of the ablation energy. In the illustrated embodiment, the frequency of the ablation energy is represented in GHz, and the power of the ablation energy is represented in Watts. The second panel 238 further includes an ablation activation/deactivation control 250 that can be clicked to initiate delivery of the ablation energy and cease delivery of the ablation energy. Thus, clicking the control 250 to initiate delivery of the stimulation energy will output ablation parameters (i.e., electrode combination, frequency, and power) to the ETS 34, which will in turn, apply the ablation energy to the electrodes in accordance with the ablation parameters. Manipulation of the previously described controls 240-248 will modify the ablation parameters transmitted to the ETS 34, which will in turn, modify the characteristics of the ablation energy applied by the ETS 34 to the electrodes.

Figure 14:
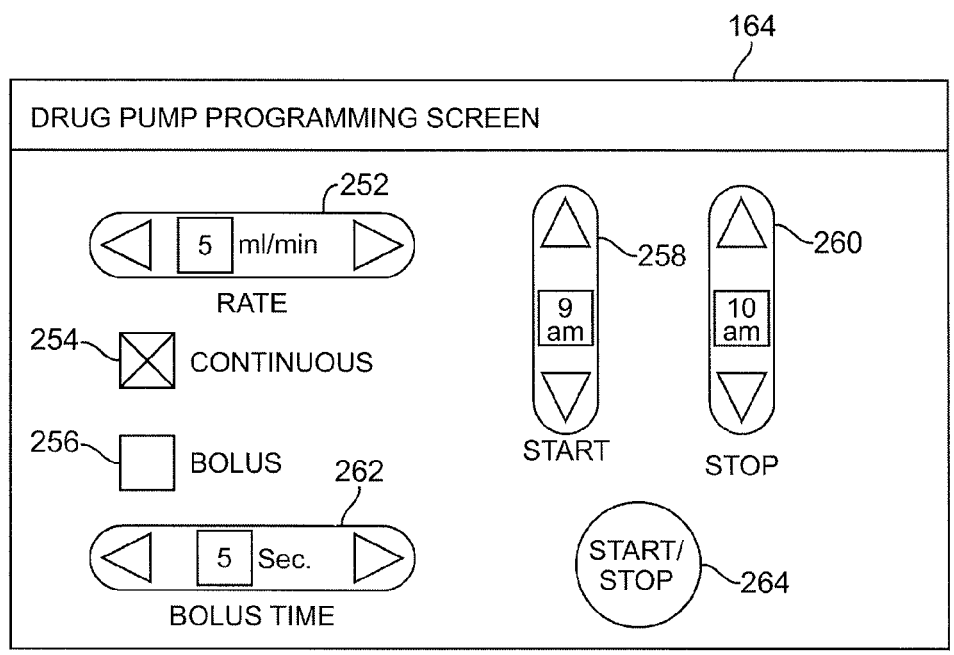
FIG. 14 is an exemplary drug pump programming screen generated by the CPS of FIG. 7.

Referring to FIG. 14, the drug pump programming screen 164 enables set(s) of drug delivery parameters to be transmitted from the CPS 42 to an implanted drug pump (shown in FIG. 2), which can be either intrathecal, epidural, or peripheral, to administer drugs to enhance the effects of the stimulation, promote tissue regeneration, prevent progression of the disease state, and/or aid in alleviating pain and inflammation. In optional embodiments, the efficacy of other medical devices, such as sensors for sensing symptoms or conditions that may indicate a needed treatment, can be tested by the CPS 42.

To this end, the programming screen 164 includes a flow rate control 252, the right arrow of which can be clicked to incrementally increase the flow rate of the drug output by the drug pump, and the left arrow of which can be clicked to incrementally decrease the flow rate of the drug output by the drug pump. The programming screen 164 further includes a continuous drug delivery box 254, the clicking of which programs the drug pump to continuously deliver the drug, and a bolus drug delivery box 256, the clicking of which programs the drug pump to deliver the drug as a bolus. Notably, much of this functionality may also be contained in a patient drug pump controller (not shown).

The programming screen 164 further includes a start time control 258 for continuous delivery, the upper arrow of which can be clicked to incrementally increase the start time of the drug delivery, and the lower arrow of which can be clicked to incrementally decrease the start time of the drug delivery. The programming screen 164 further includes a stop time control 260 for continuous delivery, the upper arrow of which can be clicked to incrementally increase the stop time of the drug delivery, and the lower arrow of which can be clicked to incrementally decrease the stop time of the drug delivery. Alternatively, the programming screen 164 comprises a continuous deliver control (not shown) that continuously delivers the drug 24 hours/day at a predetermined delivery rate. The programming screen 164 further includes a bolus time control 262, the left arrow of which can be clicked to incrementally decrease the bolus time of the drug delivery, and the right arrow of which can be clicked to incrementally increase the bolus time of the drug delivery.

The programming screen 164 further includes a drug delivery activation/deactivation control 264 that can be clicked to initiate delivery of the drug and cease delivery of the drug. Thus, clicking the control 264 to initiate delivery of the stimulation energy will output drug delivery parameters to the drug pump, which will in turn, delivery the drug in accordance with the drug delivery parameters. Manipulation of the previously described controls 252-262 will modify the drug delivery parameters transmitted to the ETS 34, which will in turn, modify the characteristics of the drug delivery output by the drug pump.

It should be noted that the various foregoing controls for adjusting features can be substituted for other actuators, such as dials, buttons, etc.

Rather than manually testing/trialing the different IPGs 18, as described above, the therapeutic comparative analysis module 140 can be activated to automatically test/trial the IPGs 18. In this case, the module 140 will automatically operate the ETS 34 in the first stimulation energy delivery mode to emulate the first IPG 18(1), then operate the ETS 34 in the second stimulation energy delivery mode to emulate the second IPG 18(2), and then operate the ETS 34 to operate the ETS 34 in the third stimulation deliver mode to emulate the third IPG 18(3). Based on patient or sensor feedback, the module 140 will select the IPG 18 that provides the patient with the best therapy. In an alternative embodiment, this automated process can be randomly performed as a blind trial to remove any bias from the patient or clinician.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:
1. A programmer for multimodal neurostimulator, comprising:
 a user interface having a monitor and an input device;
 a processor capable of generating a first programming screen for a first neurostimulator type for display on the monitor, and generating a second programming screen for a second neurostimulator type for display on the monitor;

wherein the first programming screen is capable of allowing a first set of stimulation parameters to be defined via the input device for the first neurostimulator type, and the second programming screen is capable of allowing a second set of stimulation parameters to be defined for the second neurostimulator type; and output circuitry for transmitting the first and second stimulation parameter sets.

2. A system for performing a neurostimulation trial, comprising:

one or more stimulation leads carrying a plurality of electrodes; and an external trial stimulator capable of delivering stimulation energy to the plurality of electrodes carried by the one or more stimulation leads, wherein the external trial stimulator is configurable to operate in a plurality of stimulation energy delivery modes to respectively emulate one of different neurostimulator types; and the programmer of claim 1.

3. The system of claim 2, wherein external trial stimulator is capable of delivering stimulation energy to the plurality of electrodes at a constant voltage when reconfigured to operate in a first one of the stimulation energy delivery modes, and is capable of delivering stimulation energy to the plurality of electrodes at a constant current when reconfigured to operate in a second one of the stimulation energy delivery modes.

4. The system of claim 2, wherein external trial stimulator is capable of independently delivering stimulation energy to the plurality of electrodes when reconfigured to operate in a first one of the stimulation energy delivery modes, and is capable of uniformly delivering stimulation energy to the plurality of electrodes when reconfigured to operate in a second one of the stimulation energy delivery modes.

5. The system of claim 2, wherein external trial stimulator is capable of delivering stimulation energy to the plurality of electrodes over multiple channels when reconfigured to operate in a first one of the stimulation energy delivery modes, and is capable of delivering stimulation energy to the plurality of electrodes over a single channel when reconfigured to operate in a second one of the stimulation energy delivery modes.

6. The system of claim 2, wherein external trial stimulator is capable of delivering stimulation energy to the plurality of electrodes in a multipolar manner when reconfigured to operate in a first one of the stimulation energy delivery modes, and is capable of delivering stimulation energy to the plurality of electrodes in a monopolar manner when reconfigured to operate in a second one of the stimulation energy delivery modes.

7. The system of claim 2, wherein the programmer is capable of reconfiguring the external trial stimulator to operate in one of the stimulation energy delivery modes.

8. The system of claim 7, wherein the external trial stimulator is capable of modifying the stimulation energy delivered to the plurality of electrodes during emulation of each of the different implantable neurostimulator types, and wherein the programmer is capable of controlling the modification of the stimulation energy.

9. The system of claim 7, wherein the programmer is capable of performing a therapeutic comparative analysis between the different neurostimulator types based on the emulation of the different neurostimulator types by the external trial stimulator.

10. The system of claim 7, wherein the programmer is capable of wirelessly reconfiguring the external trial stimulator.

11. The system of claim 7, wherein the programmer is capable of reconfiguring the external trial stimulator in response to a user entry.

12. The system of claim 2, wherein the one or more stimulation leads are not directly matable to the external trial stimulator, the system further comprising a lead adapter capable of mating the one or more stimulation leads to the external trial stimulator.

13. The system of claim 2, wherein the external trial stimulator is capable of delivering ablation energy to the plurality of electrodes, and wherein the programmer is capable of initiating delivery of the ablation energy from the external trial stimulator to the plurality of electrodes.

14. The programmer of claim 1, wherein the first programming screen only allows a stimulation current value to be defined via the input device for the first neurostimulator type, and the second programming screen only allows a stimulation voltage value to be defined via the input device for the second neurostimulator type.

15. The programmer of claim 1, wherein the first programming screen allows stimulation amplitude values to be independently defined via the input device for the first neurostimulator type, and the second programming screen only allows a stimulation amplitude value to be uniformly defined via the input device for the second neurostimulator type.

16. The programmer of claim 1, wherein the first programming screen allows multiple channels to be defined via the input device for the first neurostimulator type, and the second programming screen only allows a single channel to be defined via the input device for the second neurostimulator type.

17. The programmer of claim 1, wherein the first programming screen allows a multipolar configuration to be defined via the input device for the first neurostimulator type, and the second programming screen only allows a monopolar configuration to be defined via the input device for the second neurostimulator type.

18. The programmer of claim 1, wherein the processor is capable of generating a therapeutic ablation screen for display on the monitor, and wherein the therapeutic ablation screen allows a set of ablation parameters to be defined via the input device for an ablation device.

19. The programmer of claim 1, wherein the processor is capable of generating a drug delivery programming screen for display on the monitor, and wherein drug delivery programming screen allows a set of drug delivery parameters to be defined via the input device for a drug delivery device.

20. The programmer of claim 1, wherein the output circuitry comprises telemetry circuitry.

21. A method of performing a neurostimulation trial using the programmer of claim 1, comprising:

introducing one or more stimulation leads carrying a plurality of electrodes into a patient;

coupling an external trial stimulator to the one or more stimulation leads;

configuring the external trial stimulator to emulate a first neurostimulator type using the programmer while delivering stimulation energy from the external trial stimulator to the plurality of electrodes; and configuring the external trial stimulator to emulate a second neurostimulator type using the programmer while delivering stimulation energy from the external trial stimulator to the plurality of electrodes.

22. The method of claim 21, wherein the external trial stimulator is operated to deliver the stimulation energy to the plurality of electrodes at a constant voltage to emulate the first neurostimulator type, and is operated to deliver the stimulation energy to the plurality of electrodes at a constant current to emulate the second neurostimulator type.

23. The method of claim 21, wherein the external trial stimulator is operated to independently deliver the stimulation energy to the plurality of electrodes to emulate the first neurostimulator type, and is operated to uniformly deliver the stimulation energy to the plurality of electrodes to emulate the second neurostimulator type.

24. The method of claim 21, wherein the external trial stimulator is operated to deliver the stimulation energy to the plurality of electrodes over a multiple of channels to emulate the first neurostimulator type, and is operated to deliver the stimulation energy to the plurality of electrodes over a single channel to emulate the second neurostimulator type.

25. The method of claim 21, wherein the external trial stimulator is operated to deliver the stimulation energy to the plurality of electrodes in a multipolar manner to emulate the first neurostimulator type, and is operated to deliver the stimulation energy to the plurality of electrodes in a monopolar manner to emulate the second neurostimulator type.

26. The method of claim 21, further comprising modifying the stimulation energy delivered from the external trial stimulator to the plurality of electrodes during emulation of each of the first and second neurostimulator types.

27. The method of claim 21, further comprising performing a therapeutic comparative analysis between the first and second neurostimulator types based on the emulation of the first and second neurostimulator types by the external trial stimulators.

28. The method of claim 27, further comprising:
selecting one of the first and second neurostimulator types based on the therapeutic comparative analysis; and
permanently implanting a neurostimulator corresponding to the selected neurostimulator type into the patient.

* * * * *